US005952346A

United States Patent [19]

Heitsch et al.

[11] Patent Number: 5,952,346

[45] Date of Patent: Sep. 14, 1999

[54] USE OF NON-PEPTIDE BRADYKININ ANTAGONISTS FOR THE TREATMENT OR PREVENTION OF ALZHEIMER'S DISEASE

[75] Inventors: Holger Heitsch, Mainz-Kastel; Klaus Wirth, Kriftel; Gabriele Wiemer, Kronberg, all of Germany

[73] Assignee: Hoechst Marion Roussel Deutschland GmbH, Frankfurt am Main, Germany

[21] Appl. No.: 08/949,495

[22] Filed: Oct. 14, 1997

[30] Foreign Application Priority Data

| | | | |
|---|---|---|---|
| Oct. 14, 1996 | [DE] | Germany | 196 42 290 |
| Jul. 8, 1997 | [DE] | Germany | 197 29 140 |

[51] Int. Cl.$^{6}$ .......................... A61K 31/47; A61K 31/44; A61K 31/415; A61K 31/505

[52] U.S. Cl. .......................... 514/311; 514/314; 514/367; 514/299; 514/300; 514/247; 514/259; 514/396; 514/399; 514/415; 514/395

[58] Field of Search .................................... 514/311, 314, 514/367, 299, 300, 247, 259, 396, 379, 415, 395

[56] References Cited

U.S. PATENT DOCUMENTS

| | | | |
|---|---|---|---|
| 5,212,182 | 5/1993 | Musser et al. | 514/314 |
| 5,216,165 | 6/1993 | Mobilio et al. | 546/160 |
| 5,385,915 | 1/1995 | Buxbaum et al. . | |
| 5,438,064 | 8/1995 | Mobilio et al. | 514/313 |

FOREIGN PATENT DOCUMENTS

| | | |
|---|---|---|
| 0 622 361 A1 | 11/1994 | European Pat. Off. . |
| WO96/04251 | 2/1996 | WIPO . |
| WO96/13485 | 5/1996 | WIPO . |
| WO 97/32585 | 9/1997 | WIPO . |

OTHER PUBLICATIONS

Roth et al., Die Stereochemie sigmatroper 1.5–Wasserstoffverschiebungen, Chem. Ber., vol. 103: 426–439 (1970).

Kïnig et al., Eine neue Amid–Schutzgruppe, Chem. Ber., vol. 103:2041–2051 (1970).

König et al., Umlagerung von quartären Allyl–, Benzyl–und Propargyl–hydraziniumsalzen, Chem. Ber., vol. 103: 2052–2061 (1970).

Rogers, J., Inflammation as a Pathogenic Mechanism in Alzheimer's Disease, Arzneim.–Forsch./Drug Res., vol. 45(1): 439–442 (1995).

Asano et al., The identification of an orally active, nonpeptide bradykinin $B_2$ receptor antagonist, FR173657, British Journal of Pharmacology, vol. 120: 617–624 (1997).

Nitsch et al., Regulation of APP Processing, Potential for the Therapeutical Reduction of Brain Amyloid Burdenthuα , Annals New York Academy of Sciences, vol. 77: 175–182 (1996).

Huang et al., Increased Inositol 1,4,5–Trisphosphate Accumulation Correlates with an Up–Regulation of Bradykinin Receptors in Alzheimer's Disease, Journal of Neurochemistry, vol. 64(2): 761–766 (1995).

Peterson et al., Altered Response of Fibroblasts From Aged and Alzheimer Donors to Drugs that Elevate Cytosolic Free Calcium, Neurobiology of Aging, vol. 9: 261–266 (1988).

Racchi et al., Bradykinin Induced Amyloid Precursor Protein Secretion In Fibroblasts From Alzheimer's Disease, Down's Syndrome And Control Donors, Soc. Neurosci. Abst., p. 1944, Nov. 1966.

Griesbacher et al., Fr173657, A New, Potent And Selective Nonpeptide Bradykinin Antagonist: In Vivo Studies, Naunyn–Schmiedeberg's Arch. Pharmacol., page r6, Sep. 1996.

*Primary Examiner*—Theodore J. Criares
*Attorney, Agent, or Firm*—Finnegan, Henderson, Farabow, Garrett & Dunner, L.L.P.

[57] ABSTRACT

The invention relates to the use of non-peptide bradykinin antagonists for the production of pharmaceuticals for the prevention and treatment of Alzheimer's disease. Suitable Compounds are non-peptide bradykinin antagonists which inhibit the actions of the Alzheimer's protein amyloid (β/A4) in isolated endothelial cells, such as for example, fused heterobicyclic fluoroalkyl derivatives.

5 Claims, No Drawings

USE OF NON-PEPTIDE BRADYKININ ANTAGONISTS FOR THE TREATMENT OR PREVENTION OF ALZHEIMER'S DISEASE

The present invention relates to the use of non-peptide bradykinin antagonists for the production of pharmaceuticals for the treatment or prevention of Alzheimer's disease.

Bradykinin and related peptides are potent vasoactive, endogenous substances which produce inflammation and pain. EP-A 622 361, U.S. Pat. No. 5,212,182, U.S. Pat. No. 5,216,165, U.S. Pat. No. 5,438,064, WO 96 04251, WO 96 13485, German Patent Application P 19610784.9 and the still unpublished German Patent Application P 19620508.5 disclose substituted, fused heterobicyclic systems and their use as bradykinin receptor antagonists and as compositions for the control of conditions which are mediated, induced or supported by bradykinin.

Increasingly, the importance of localized inflammation is recognized for the destructive changes in the brain of patients with Alzheimer's disease. Inflammatory changes lead to chronicity and to the continuing destruction of the brain and thus severe dementia (J. Rogers, Inflammation as a pathogenic mechanism in Alzheimer's disease, Arzneimittelforschung 1995; 45 (3A), 439–442). It was previously unknown that bradykinin, a strongly inflammatory mediator in the periphery, could play a part in Alzheimer's disease. This is to be attributed to the fact that there was no evidence of the release of bradykinin in the brain of patients with Alzheimer's disease. The inactive high molecular weight precursors from which bradykinin is released cannot pass into the brain (neuronal tissue) without problems, namely because of the low permeability of the blood-brain barrier.

Our investigations have shown that the Alzheimer's protein β/A4 can release bradykinin from the endothelium of vascular walls. The essential pathological changes of Alzheimer's disease are ascribed to the Alzheimer protein β/A4. See, for example, C. L. Joachim and D. J. Selkoe, The seminal role of beta-amyloid in the pathogenesis of Alzheimer disease, Alzheimer Dis. Assoc. Disord., 1992 Spring, vol. 6(1), pp. 7–34. Once the release of the inflammatory bradykinin is shown by a mechanism which is specific for Alzheimer's disease, bradykinin becomes a pathophysiological factor of the first rank, by which the Alzheimer's protein can mediate its destructive action. This applies especially with respect to inflammation, whose importance for the destructive changes is increasingly recognized, since bradykinin is one of the most potent endogenous inflammatory substances.

Beside the inflammatory action, bradykinin additionally has two further properties through which it can contribute to the destructive changes in Alzheimer's disease. Bradykinin stimulates CNS neurons. On strong stimulation, this leads to calcium overloading of the affected cells, with subsequent cell death. On moderate stimulation, bradykinin only becomes a false transmitter, which inadequately stimulates neurons. Such an inadequate stimulation of neurons, which should actually not be stimulated at all, can sensitively interfere with the process of information processing in the brain and contribute to the typical brain function disorders, the latter mechanism, caused by moderate stimulation, appearing to be reversible.

As a vasoactive mediator, bradykinin, as is known, increases the permeability of the blood-brain barrier. This results in the fact that the precursors of bradykinin can first pass from the blood vessels into the brain in order to display their destructive action there.

Surprisingly, it has now been found that non-peptide bradykinin antagonists of this structural type are moreover suitable agents for the treatment or prevention of Alzheimer's disease. This relates both to the intention to prevent progress of the disease, and to treat symptoms which have already occurred. Moreover, the above-mentioned bradykinin antagonists on preventive administration are also suitable to prevent the origination of Alzheimer's disease if in the future it should be possible by means of suitable diagnostic measures to predict a later outbreak of the disease.

Suitable compounds are non-peptide bradykinin antagonists which inhibit the actions of the Alzheimer's protein amyloid (β/A4) in isolated endothelial cells.

Suitable non-peptide bradykinin antagonists are, inter alia, the compounds of the formula (I)

(I)

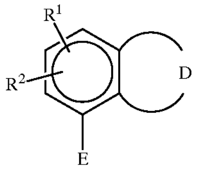

in which the symbols have the following meanings:

D is 1) a radical of the formula (II)

(II)

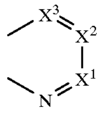

or 2) a radical of the formulae (III) to (VI)

(III)

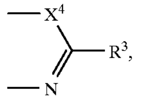

(IV)

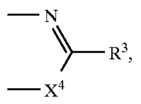

(V)

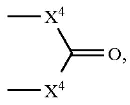

, and (VI)

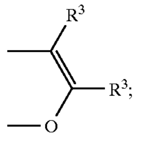

E is 1) a radical of the formula (VII)

(VII)

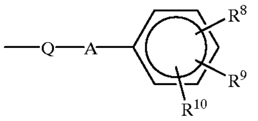

or 2) hydrogen, halogen, $(C_1-C_4)$-alkyl, $(C_1-C_4)$-alkylthio or $(C_1-C_4)$-alkoxy, where in the last 3 radicals 1 or more hydrogen atoms can be replaced by fluorine;

$X^1$ is nitrogen or C—$R^4$;

$X^2$ is nitrogen or C—$R^5$;

$X^3$ is nitrogen or C—$R^5$;

$X^4$ is independently oxygen, sulfur, nitrogen or N—$R^7$;

$R^1$ and $R^2$ are identical or different and are hydrogen, halogen, $(C_1-C_4)$-alkyl or $(C_1-C_4)$-alkoxy;

$R^3$ is independently hydrogen, halogen, $(C_1-C_6)$-alkyl, $(C_6$-$C_{12})$-aryl, $(C_1-C_3)$-alkyl-$(C_6-C_{12})$-aryl, $(C_3-C_5)$-alkenyl, $(C_1-C_4)$-alkoxy or $CO_2R^{11}$;

$R^4$ is hydrogen, halogen, $(C_1-C_4)$-alkyl, hydroxyl, $(C_1-C_4)$-alkylthio, amino, $(C_1-C_4)$-alkylamino, $(C_1-C_4)$-dialkylamino, $(C_1-C_4)$-alkoxy, in which the alkyl part of any of the preceding substituents is optionally substituted by hydroxyl, $(C_1-C_4)$-alkoxy, amino and $(C_1-C_4)$-alkylamino, or $(C_6-C_{12})$-aryl, optionally substituted by $(C_1-C_4)$-alkyl or $CO_2R^{11}$;

$R^5$ is 1) hydrogen, $(C_1-C_4)$-alkyl or

2) 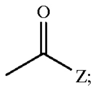

$R^6$ is 1) hydrogen, halogen, $(C_1-C_4)$-alkyl, hydroxcyl, $(C_1-C_4)$-alkylthio, amino, $(C_1-C_4)$-alkylamino, $(C_1-C_4)$-dialkylamino, $(C_1-C_4)$-alkoxy, in which the alkyl part of any of the preceding substituents is optionally substituted by hydroxyl, $(C_1-C_4)$-alkoxy, amino and $(C_1-C_4)$-alkylamino, or $(C_6-C_{12})$-aryl, optionally substituted by $(C_1-C_4)$-alkyl or $CO_2R^{11}$; or 2) a radical of the formula (VIII)

(VIII)

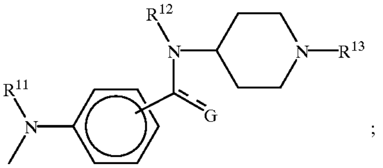

;

$R^7$ is independently $(C_1-C_4)$-alkyl, $(C_1-C_{12})$-aryl or $(C_1-C_3)$-alkyl-$(C_1-C_{12})$-aryl;

$R^8$ and $R^9$ are identical or different and are hydrogen, halogen, $(C_1-C_3)$-alkyl or $(C_1-C_3)$-alkoxy;

A is $(C_1-C_3)$-alkanediyl;

Q is O or $NR^{11}$;

$R^{10}$ is a radical of the formula (IX)

(IX)

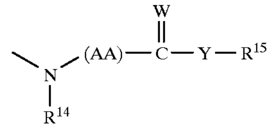

wherein W is oxo or sulfur;

$R^{11}$ is independently hydrogen or $(C_1-C_4)$-alkyl;

$R^{14}$ is independently hydrogen or $(C_1-C_4)$-alkyl;

G is oxo or 2 single-bonded hydrogen atoms $R^{12}$ is, if G is oxo, hydrogen and if G is 2 single-bonded hydrogen atoms, hydrogen or $R^{16}CO$;

$R^{13}$ is $(C_1-C_4)$-alkyl, $(C_3-C_7)$-cycloalkyl, —$(CH_2)_m$-$(C_3-C_7)$-cycloalkyl, —$(CH_2)_m$—$CON(R^{11})_2$, or

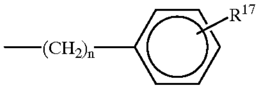

;

m and n are, identically or differently, a number from 0–6;

AA is an amino acid such as methionine, alanine, phenylalanine, 2-chlorophenylalanine, 3-chlorophenylalanine, 4-chlorophenyl-alanine, 2-fluorophenylalanine, 3-fluorophenylalanine, 4-fluorophenylalanine, tyrosine, o-methyltyrosine, β-(2-thienyl)-alanine, glycine, cyclohexylalanine, leucine, isoleucine, valine, norleucine, phenylglycine, serine, cysteine, aminopropionic acid or aminobutyric acid;

Y is 1) $(C_2-C_5)$-alkenediyl,

2) $(C_1-C_8)$-alkanedlyl,

3) $(C_3-C_{10})$-cycloalkanediyl or

4) —$(CH_2)_p$-$T_o$—$(CH_2)_q$-, where 1) to 4) can optionally be substituted by one or more identical or different radicals such as O—$R^{18}$, $NO_2$, CN, $CO_2R^{11}$, $SO_3R^{18}$, $NR^{20}R^{21}$, $SO_2NR^{20}R^{21}$, $CONR^{20}R^{21}$;

T is O, $NR^{21}$ or S;

o is a number 0 or 1;

p and q are identical or different and denote a number from 0 to 6;

$R^{15}$ independently is 1) hydrogen,

2) $(C_1-C_5)$-alkyl,

3) $(C_6-C_{10})$-aryl or

4) $(C_1-C_9)$-heteroaryl, where 3) and 4) can optionally be substituted by one or more identical or different groups, such as halogen, CN, $NO_2$, $(C_1-C_5)$-alkylthio, $NR^{20}R^{21}$, $CO_2R^{19}$, $SO_3R^{18}$, $SO_2NR^{20}R^{21}$, $SO_2R^{18}$, O—$R^{18}$, $NR^{20}CO$—$R^{15}$, $(C_1-C_6)$-alkyl, $(C_6-C_{10})$-aryl, $(C_2-C_5)$-alkenyl or $(C_1-C_5)$-alkoxy, where the last four radicals can optionally be partly or completely substituted by halogen;

$R^{16}$ is independently hydrogen, $(C_1-C_4)$-alkyl, $(C_1-C_1$, 1)-aryl. $(C_1-C_4)$-alkyl-$(C_6-C_{12})$-aryl or perfluoro-$(C_1-C_4)$-alkyl;

$R^{17}$ is hydrogen, halogen, $(C_1-C_4)$-alkyl, $(C_1-C_4)$-alkoxy, perfluoro-$(C_1-C_4)$-alkyl, $NO_2$, OH, $NH_2$, $CON(R^{16})_2$ or $NR^{16}CON(R^{16})_2$;

$R^{18}$, $R^{19}$ and $R^{20}$ are each identical or different and are hydrogen, $(C_1-C_5)$-alkyl, $(C_3-C_5)$-alkenyl, $(C_6-C_{12})$-aryl-$(C_1-C_3)$-alkyl, $(C_3-C_{10})$-cycloalkyl, $(C_3-C_{10})$-cycloalkyl-$(C_1-C_3)$-alkyl, C(O)—O—$(C_1-C,)$-alkyl or C(O)—NH—$(C_1-C_5)$-alkyl;

$R^{21}$ is independently hydrogen, C(O)—O—($C_1$–$C_5$)-alkyl or C(O)—O—($C_1$–$C_3$)-alkyl-($C_6$–$C_{10}$)-aryl;

Z is —N($R^{14}$)($R^{22}$);

$R^{22}$ is

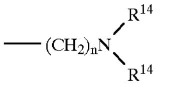

or

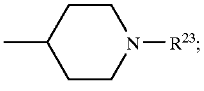

$R^{23}$ is ($C_1$–$C_4$)-alkyl,

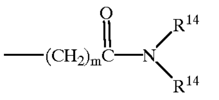

or

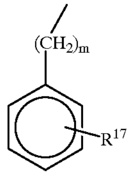

;

or a physiologically tolerable salt thereof.

Alkyl and alkenyl can be straight-chain or branched. The same applies to radicals derived therefrom such as alkoxy.

Alkenyl is mono- or polyunsaturated groups such as 1,4-butadienyl, 8,11-heptadienyl, 8,11,14-heptatrienyl and butenyl. The same applies to cycloalkenyl.

Cycloalkyl is mono- or bicyclic groups such as cyclopropyl, cyclopentyl, cyclohexyl, bicyclononyl. The same applies to cycloalkenyl.

($C_6$–$C_{12}$)-aryl is, for example, phenyl, naphthyl or biphenylyl, preferably phenyl. The same also applies to radicals derived therefrom such as aralkyl.

Halogen (Hal) is fluorine, chlorine, bromine or iodine, preferably chlorine or fluorine.

($C_1$–$C_9$)-Heteroaryl is understood as meaning radicals which are derived from phenyl or naphthyl, in which one or more CH groups are replaced by N and/or in which at least two adjacent CH groups are replaced by S, NH or O (with formation of a five-membered aromatic ring). In addition, one or both atoms of the condensation site of bicyclic radicals (such as indolizinyl) can also be nitrogen atoms.

Heteroaryl is considered, in particular, as furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl, benzopyranonyl, coumarinyl, pyranonyl, furandionyl.

Physiologically tolerable salts of compounds of the formula (I) are understood as meaning both their organic and inorganic salts, such as are described in Remington's Pharmaceutical Sciences (A. R. Gennard Editor, Mack Publishing Co., Easton PA, 17th Edition, page 1418 (1985)), the disclosure of which is specifically incorporated by reference herein. On account of the physiological and chemical stability and the solubility, acidic groups, inter alia, sodium, potassium, calcium and ammonium salts, are preferred; for basic groups, inter alia, salts of hydrochloric acid, sulfuric acid, phosphoric acid or of carboxylic acids or sulfonic acids, such as acetic acid, citric acid, benzoic acid, maleic acid, fumaric acid, tartaric acid and p-toluenesulfonic acid, are preferred.

Suitable non-peptide bradykinin antagonists and their synthesis are described, for example, in the Patent Applications EP-A 622 361, U.S. Pat. No. 5,212,182, U.S. Pat. No. 5,216,165, U.S. Pat. No. 5,438,064, WO 9604251, WO 9613485, German Patent Application P 19610784.9 and also in the still unpublished German Patent Application P 19620508.5, the disclosures of which are specifically incorporated by reference herein.

The German Patent Application P 19610784.9 describes heterocyclic fluoroalkyl derivatives and fluoroalkoxy derivatives of the formula (IA)

(IA)

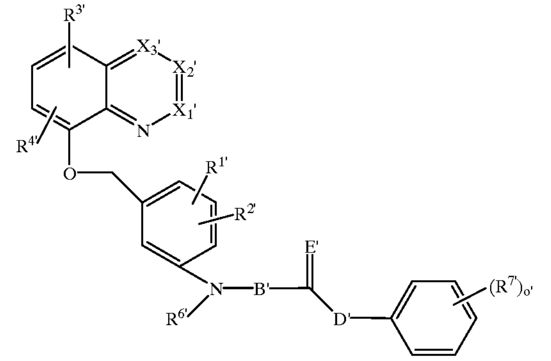

in which the symbols have the following meaning:

a) $X_1'$–$X_3'$, identically or differently, are N or $CR^5$;

b) $R^{1'}$ and $R^{2'}$, identically or differently, are

1) Hor 2) halogen;

c) $R^{3'}$ and $R^{4'}$, identically or differently, are

1) H 2) halogen 3) ($C_1$–$C_5$)-alkyl or 4) ($C_2$–$C_5$)-alkenyl;

d) $R^{5'}$ is

1) H

2) Halogen 3) ($C_1$–$C_6$)-alkyl

4) O—$R^{6'}$

5) S—$R^{5'}$

6) $NHR^{6'}$ 7) ($C_6$–$C_{12}$)-aryl 8) ($C_6$–$C_{12}$)-aryl-($C_1$–$C_3$)-alkyl 9) —C(O)—$OR^{6'}$ or

10)—C(O)—H where 3), 7) and 8) and can optionally be substituted by one or more groups such as, for example, $OR^{6'}$, $SR^{6'}$, $NO_2$, CN, $NHR^{6'}$, halogen;

e) $R^{6'}$ is independently

1) H 2) ($C_1$–$C_5$)-alkyl 3) ($C_3$–$C_5$)-alkenyl or 4) ($C_6$–$C_{12}$)-aryl-($C_1$–$C_3$)-alkyl;

e)' $R^{8'}$ is independently

1) H 2) ($C_1$–$C_5$)-alkyl 3) ($C_3$–$C_5$)-alkenyl or 4) ($C_6$–$C_{12}$)-aryl-($C_1$–$C_3$)-alkyl;

f) $R^{7'}$ is independently 1) ($C_1$–$C_5$)-alkyl, where hydrogen is partly or completely replaced by fluorine or chlorine or 2) ($C_1$–$C_5$)-alkoxy, where hydrogen is partly or completely replaced by fluorine or chlorine;

g) B is an aminocarboxylic acid, e.g. methionine, alanine, phenylalanine, 2-chlorophenylalanine, 3-chlorophenylalanine, 4-chlorophenylalanine, 2-fluorophenylalanine, 3-fluoro-phenylalanine, 4-fluorophenylalanine, tyrosine, O-methyl-tyrosine, β-2-thienyl)alanine, glycine, cyclohexylalanine, leucine, isoleucine, valine, norleucine or phenylglycine, serine or cysteine, aminopropionic acid, aminotutyric acid;

h) D' is

1) $(C_2-C_5)$-alkenediyl or

2) $-(CH_2)_{n'}-Y'_{p'}-(CH_2)_{m'}$;

i) E is

1) O or

2) S;

j) Y is

1) O

2) S or

3) NR';

k) n' and m', identically or differently, are a number from 0–3;

l) o is a number from 1–3;

m) p is a number 0 or 1;

or a physiologically tolerable salt thereof.

The compounds of the formula (IA) are prepared by a process which comprises:

a) deprotonating a compound of the formula (XII), (XII)

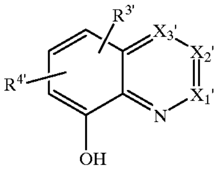

in which $X_1'-X_3'$ and $R^{3'}$ and $R^{4'}$ are as defined above in formula (IA), with $Cs_2CO_3$ or $K_2CO_3$ in an inert solvent, preferably DMF or N-methylpyrrolidine, and reacting at room temperature with a compound of the formula (XIII)

(XIII)

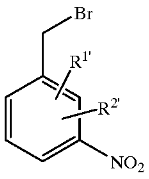

in which $R^{1'}$ and $R^{2'}$ are as defined above in formula (IA);

b) reducing the compound thus obtained of the formula (XIV)

(XIV)

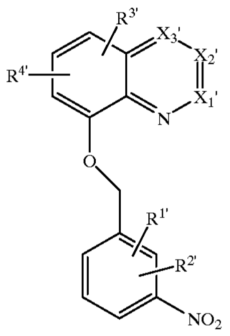

in which $R^{1'}$, $R^{2'}$, $R^{3'}$, $R^{4'}$, $X_1'$, $X_2'$ and $X_3'$ are as defined above in formula (IA), with the aid of transition metal halides, preferably $SnCl_2$, $FeCl_3$, to a compound of the formula (XV)

(XV)

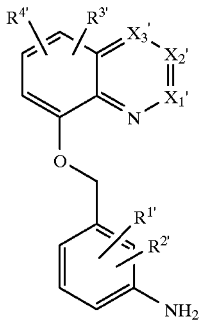

in which $R^{1'}$, $R^{2'}$, $R^{3'}$, $R^{4'}$, $X_1'$, $X_2'$ and $X_3'$ are as defined above in formula (IA);

c) reacting a compound of the formula (XV) with ;activated, suitably protected aminocarboxylic acid derivatives of B' (B'-Prot), preferably the acid chlorides of the phthaloyl-protected aminocarboxylic acid derivatives of B', in inert solvents such as, for example, NMP, optionally by addition of DMAP, and thus obtaining a compound of the formula (XVI)

(XVI)

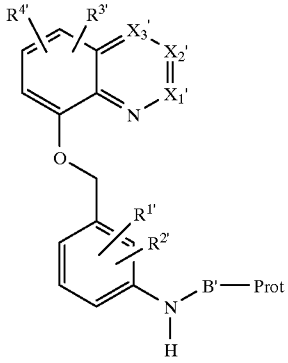

in which B', $R^{1'}$, $R^{2'}$, $R^{3'}$, $R^{4'}$, $X_1'$, $X_2'$ and $X_3'$ are as defined above in formula (IA), and Prot is an amino protective group, as described in T. W. Greene "Protective Groups in organic Synthesis", Publishers John Wiley, 2nd Edition 1991, the disclosure of which is specifically incorporated by reference herein, e.g. phthaloyl, benzyl or paramethoxybenzyl;

d) reacting a compound of the formula (XVI), after the action of alkali metal hydrides, alkali metal carbonates or alkoxides in inert solvents, preferably DMF or NMP, followed by a treatment with $R^{6'}X$, where $R^{5'}$ is as defined above in formula (IA) and X is a leaving group, e.g. halogen, mesylate or tosylate, a compound of the formula (XVII) being obtained (XVII)

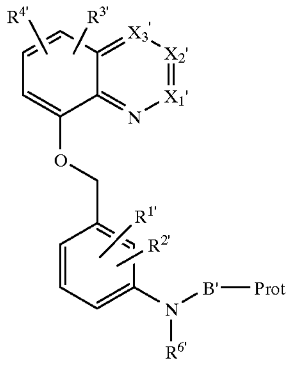

in which B', $R^{1'}$, $R^{2'}$, $R^{3'}$, $R^{4'}$, $R^{6'}$, $X_1'$, $X_2'$ and $X_3'$ are as defined above in formula (IA) and Prot is as defined above in formula (XVI);

e) for the removal of the protective group (Prot) from the compound of the formula (XVII), in the case of the phthaloyl group preferably reacting with hydrazine in alcohols as solvents at temperatures between room temperature and the boiling point, preferably at room temperature, a compound of the formula (XVIII) being obtained (XVIII)

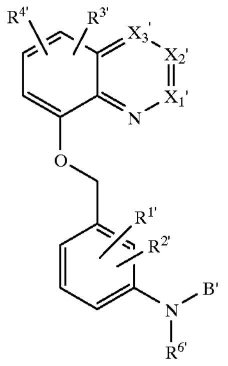

in which B', $R^{1'}$, $R^{2'}$, $R^{3'}$, $R^{4'}$, $R^{6'}$, $X_1'$, $X_2'$ and $X_3'$ are as defined above in formula (IA) and Prot is as defined above in formula (XVI);

$f_1$) reacting a compound of the formula (XVIII) with activated carboxylic acid derivatives of the formula (XIX), (XIX)

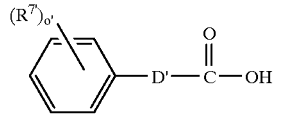

in which $R^{7'}$, o and D are as defined above in formula (IA), preferably their acid chlorides or carboxylic acids of the formula (XIX) activated by reagents such as are used in peptide synthesis, or $f_2$) reacting a compound of the formula (XVIII) with an amine or an alcohol of the formula (XX)

(XX)

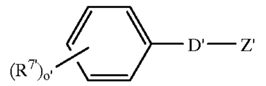

in which $R^{7'}$, o and D are as defined above in formula (IA) and Z' is OH or $NH_2$, preferably at temperatures between 0° C. and room temperature in inert solvents, preferably dichloromethane or dimethoxyethane, first, however, the compound of the formula (XVIII) or (XX) being allowed to react with a doubly activated carbonyl compound to form the urea or urethane group, e.g. with carbodiimides, phosgene or chlorocarbonic acid esters, preferably phosgene and carbonyldiimidazole, or $f_3$) reacting a compound of the formula (XVIII) with an appropriate isocyanate or isothiocyanate, preferably at temperatures between 0° C. and room temperature in inert solvents, preferably dichloromethane or dimethoxyethane, and g) converting the compound of the formula (IA) obtained into a physiologically tolerable salt thereof, if appropriate, according to known methods.

The conversion to the bromomethyl compound is carried out by reaction of the corresponding methyl derivative with N-bromo-succinimide, dibromohydantoin or bromine in inert solvents, preferably bromobenzene or cyclohexane at temperatures from 60° C. up to the boiling point.

It is possible to use as a coupling reagent all possible activating reagents used in peptide synthesis, see, for example, Houben-Weyl, Methoden der organischen Chemie (Methods of Organic Chemistry), Volume 15/2, Georg Thieme Verlag, Stuttgart 1974, the disclosure of which is specifically incorporated by reference herein, but in particular carbodiimides such as, for example, N,N'-dicyclohexyicarbodiimide, N,N'-diisopropylcarbodiimide or N-ethyl-N'-(3-dimethylaminopropyl)-carbodiimide. Coupling can be carried out directly here by addition of carboxylic acid derivative with the activating reagent and, if appropriate, an additive such as, for example, 1-hydroxybenzotriazole (HOBt) (W. König, specifically incorporated by reference herein, or 3-hydroxy4-oxo-3,4-dihydrobenzotriazine (HOObT) (W. König, R. Geiger, (Chem. Ber. 103, 2054 (1970)), the disclosure of which is specifically incorporated by reference herein, or else the preactivation of the carboxylic acid derivative as a symmetrical anhydride or HOBt or HOObT ester can take place separately and the solution of the activated species can be added to the amine in a suitable solvent.

The coupling and activation of the amino acid derivatives using one of the abovementioned activating reagents can be carried out in dimethylformamide, N-methylpyrrolidone or methylene chloride or a mixture of the solvents mentioned.

Instead of the phthaloyl group, it is also possible to use protective groups which protect both protons of the amino group, e.g. 2 benzyl groups.

The still unpublished patent application P 19620508.5 describes sulfur-containing heterocyclic compounds of the formula (IB)

(IB)

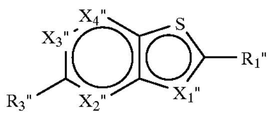

in which the symbols have the following meanings:

a) one of the radicals $X_1''$, $X_2''$ or $X_3''$ is C—O—$R^{2''}$ and the other $X_1''$, $X_2''$, $X_3''$ and $X_4''$ in each case are then, identically or differently, 1 ) N or

2) $CR^{1''}$;

b) $R^{1''}$ and $R^{3''}$, identically or differently, are b) $R^{1''}$ and $R^{3''}$, identically or differently, are

1) H 2) halogen

3) $(C_1–C_6)$-alkyl

4) O—$R^{6''}$

5) S—$R^{6''}$

6) $NHR^{6''}$

7) $(C_6–C_{12})$-aryl

8) $(C_6–C_{12})$-aryl-$(C_1–C_3)$-alkyl

9) C(O)—$OR^{5''}$

10) C(O)—H

11) $(C_2–C_5)$-alkenyl

12) $NO_2$

13) $SO_3R^{7''}$

14) CN or

15) C(O)—$NHR^{8''}$ where 3), 7), 8), and 11) can optionally be substituted by one or more groups such as C(O)—$(O)_{o''}$-$(C_1–C_5)$-alkyl, $OR^{6''}$, $SR^{7''}$, $NO_2$, CN, $NHR^{8''}$, or halogen;

c) $R^{2''}$ is a compound of the formula (XXII)

(XXII)

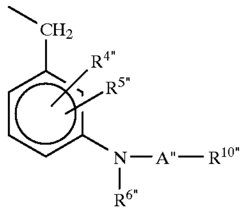

d) $R^{4''}$ and $R^{5''}$, identically or differently, are

1) H 2) halogen

3) $OR^{6''}$

4) $SR^{6''}$

5) CN or

6) $(C_1–C_5)$-alkyl;

e) $R^{6''}$, $R^{7''}$ and $R^{8''}$, identically or differently, are

1) H

2) $(C_1–C_5)$-alkyl

3) $(C_3–C_5)$-alkenyl

4) $(C_6–C_{12})$-aryl-$(C_1–C_3)$-alkyl

5) $(C_3–C_{10})$-cycloalkyl

6) $(C_3–C_{10})$-cycloalkyl-$(C_1–C_3)$-alkyl

7) C(O)—$(O)_{o''}$—$(C_1–C_3)$-alkyl or

8) C(O)—$(NH)_{o''}$—$(C_1–C_5$-alkyl;

f) A" is an aminocarboxylic acid, e.g. methionine, alanine, phenyl-alanine, 2-chlorophenylalanine, 3-chlorophenylalanine, 4-chlorophenylalanine, 2-fluorophenylalanine, 3-fluoro-phenylalanine, 4-fluorophenylalanine, tyrosine, O-methyltyrosine, β-(2-thienyl)alanine, glycine, cyclohexylalanine, leucine, isoleucine, valine, norleucine, phenylglycine, serine, cysteine, aminopropionic acid or aminobutyric acid;

9) $R^{9''}$ is

1) H

2) C(O)—$(O)_{o''}$—$(C_1–C_5)$-alkyl or

3) C(O)—$(O)_{o''}$—$(C_1–C_3)$-alkyl-$(C_6–C_{10})$aryl;

h) $R^{10''}$ is

1) —C(O)—D"—E"

2) —C(S)—D"—E"

3) —$SO_2$—D"—E" or 4) hydrogen i) D" is

1) $(C_2–C_5)$-alkenediyl

2) $(C_1–C_8)$-alkanediyl

3) —$(CH_2)_{n''}$—$Y_{o''}$—$(CH_2)_{m''}$—

4) $(C_3–C_{10})$-cycloalkanediyl

5) $(C_3–C_{10})$-cycloalkyl-$(C_1–C_3)$-alkanediyl

6) $(C_3–C_{10})$-cycloalkenediyl or

7) $(C_3–C_{10})$-cycloalkenyl-$(C_1–C_3)$-alkanediyl where 1)–7) can optionally be substituted by one or more groups such as, for example, $OR^{6''}$, $NO_2$, CN, $CO_2R^{7''}$, $NR^{8''}R^{9''}$, $SO_2R^{6''}$, $SO_2NR^{8''}R^{9''}$, $SO_3R^{7''}$ or C(O)—$NR^{8''}R^{9''}$;

j) E" is

1) H

2) $(C_1–C_{10})$-aryl or

3) $(C_1–C_9)$-heteroaryl where 2) and 3) can optionally be substituted by one or more groups such as, for example, $NR^{8''}R^{9''}$, CN, $CO_2R^{6''}$, $SO_3R^{7''}$, $NO_2$, $SO_2NR^{8''}R^{9''}$, $SO_2R^{6''}$, O—$(C_1–C_5)$-alkyl, S-$(C_1–C_5)$-alkyl, $(C_1–C_5)$-alkyl, $(C_2–C_5)$-alkenyl, where O—$(C_1–C_5)$-alkyl and $(C_1–C_5)$-alkyl can optionally be partly or completely substituted by halogen;

k) Y" is

1) O

2) S or

3) $NR^{8''}$;

I) n" and m", identically or differently, are a number from 0–6;

m) o", identically or differently, is 0 or 1; or a physiologically tolerable salt thereof.

The compounds of the formula (IB) are prepared by a process which comprises:

$a_1$) 1) acylating a compound of the formula (XXIII)

(XXIII)

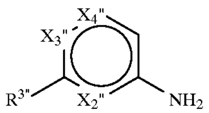

in which $R^{3''}$, $X_2''$, $X_3''$ and $X_4^{41}$ are as defined above in formula (IB), first with activated carboxylic acid derivatives, preferably their acid chlorides, using an auxiliary base, preferably triethylamine or diisopropylethylamine, at temperatures between 0–20° C.;

2) heating to boiling the compound thus; obtained of the formula (XXIV)

(XXIV)

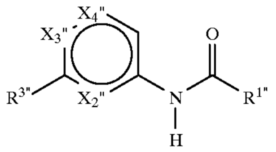

with Lawesson's reagent or preferably $P_2S_{10}$ in butyl acetate or other inert high-boiling solvents and thus obtaining a compound of the formula (XXV)

(XXV)

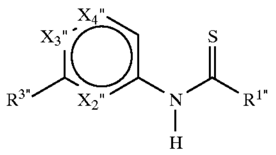

in which $R^{1''}$, $R^{3''}$, $X_2''$, $X_3^{41}$ and $X_4^{41}$ in formulae (XXIV) and (XXV) are as defined above in formula (IB), with the proviso that if $X_2''$ or $X_3''$ is C—O—$R^{2''}$, then $R^{2''}$ is not as defined above but rather is H or ($C_1$–$C_5$)-alkyl, preferably methyl or ethyl;

3) reacting the compound (XXV) thus obtained by free-radical cyclization with free radical-producing reagents, preferably $K_3Fe(CN)_6$ or $Br_2$ in inert solvents, preferably $H_2O$, at temperatures between 80–110° C. and in this way obtaining a compound of the formula (XXVI)

(XXVI)

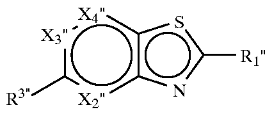

in which the radicals $R^{1''}$, $R^{3''}$, $X_2''$, $X_3^{41}$ and $X_4^{41}$ are as defined above in formula (IB), with the proviso that if $X_2''$ or $X_3^{41}$ is C—O—$R^{2''}$, then $R^{2''}$ is not as defined above but rather is H or ($C_1$–$C_5$)-alkyl, preferably methyl or ethyl;

4) reacting a compound of the formula (XXVI), in which $X_2''$ or $X_3^{41}$ is C—O—$R^{2''}$ and is as defined under 3., by ether-cleaving reagents, preferably $BBr_3$, HI/red phosphorus, HBr, $HBr/CH_3CO_2H$ in inert solvents or without solvent at temperatures between 0° C. and the boiling point, to give compounds of the formula (XXVI) in which $X^{2''}$ or $X^{3''}$ is $COR^{2''}$, wherein $R^{2''}$ is hydrogen;

or $a_2$) 1) converting a compound of the formula (XXVII)

(XXVII)

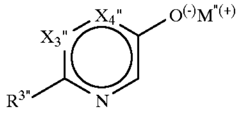

in which $R^{3''}$, $X_3^{41}$, $X_4^{4}$ are as defined above in formula (IB) and $M''$ is potassium, sodium or cesium, by successive treatment with $CO_2$ and then $NH_3$ at increased temperatures and pressures, preferably 100 atm and 200° C., into a compound of the formula (XXVIII)

(XXVIII)

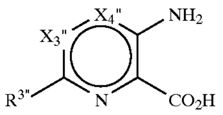

in which $R^{3''}$, $X_3^{41}$, $X_4''$ are as defined above in formula IB);

2) converting a compound of the formula (XXVIII) by diazotization and subsequent treatment with HS—$CHR^{1''}$—$CO_2H$ into a compound of the formula (XXIX)

(XXIX)

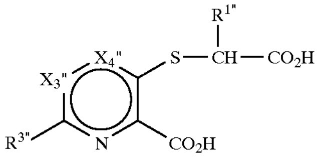

in which $R^{1''}$, $R^{3''}$, $X_3''$, $X_4''$ are as defined above in formula (IB);

3) converting a compound of the formula (XXIX) by cyclization with simultaneous decarboxylation and water elimination in inert solvents, preferably $H_2O$, or without solvent, preferably at temperatures of about 100° C., into c compound of the formula (XXX)

(XXX)

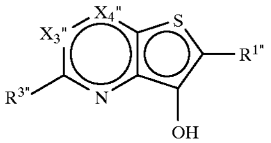

in which $R^{1''}$, $R^{3''}$, $X_3^{41}$, $X_4^{41}$ are as defined above in formula (IB);

b) deprotonating a compound of the formula (XXVI) or (XXX)

(XXVI)

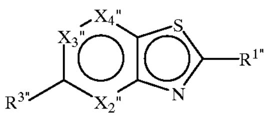

(XXX)

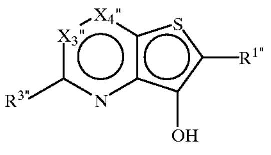

in which $X_2''$, $X_3''$, $X_4''$, $R^{1''}$ and $R^{3''}$ are as defined above in formula (IB), except that in the case of compounds of the formula (XXVI) $X_2''$ or $X_3''$=C—O—H, with $Cs_2CO_3$ or $K_2CO_3$ in an inert solvent, preferably DMF or N-methylpyrrolidine, and reacting at room temperature with a compound of the formula (XXXI)

(XXXI)

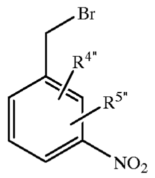

in which $R^{4"}$ and $R^{5"}$ are as defined above in formula (XXII);

c) reducing the compound thus obtained of the formula (XXXII) or (XXXII')

(XXXII)

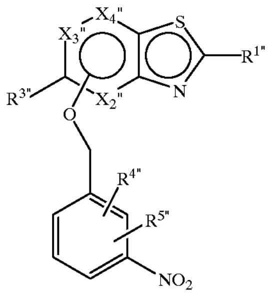

(XXXII')

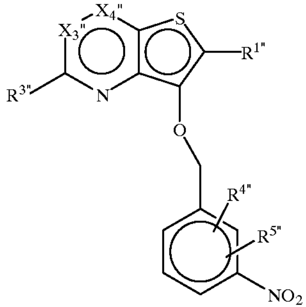

in which $R^{1"}$, $R^{3"}$, $R^{4"}$, $R^{5"}$, $X_2"$, $X_3"$, $X_4"$ are as defined above in formulae (IB) and (XXII), with the aid of transition metal halides, preferably $SnCl_2$, $FeCl_3$, to a compound of the formula (XXXIII) or (XXXIII')

(XXXIII)

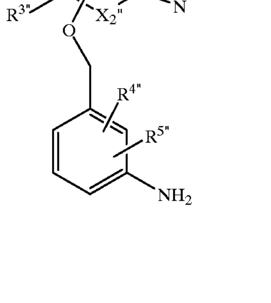

-continued (XXXIII')

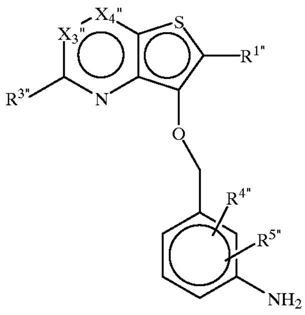

in which $R^{1"}$, $R^{3"}$, $R^{4"}$, $R^{5"}$, $X_2"$, $X_3"$ and $X_4"$ are as defined above in formulae (IB) and (XXII);

d) reacting a compound of the formula (XXXIII) or (XXXIII') with activated, suitably protected amino carboxylic acid derivatives of (A"), i.e., (A"-Prot"), preferably the acid chlorides of the phthaloyl-protected aminocarboxylic acid derivatives of A", in inert solvents such as, for example, NMP, if appropriate by addition of DMAP, and thus obtaining a compound of the formula (XXXIV) or (XXXIV')

(XXXIV)

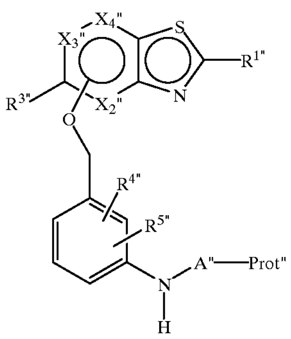

(XXXIV')

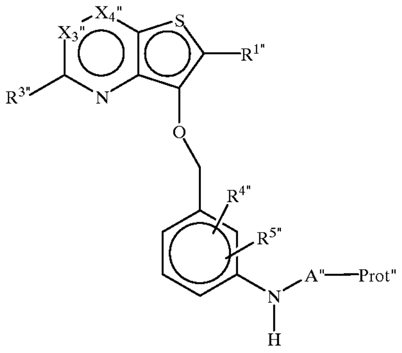

in which A", $R^{1"}$, $R^{3"}$, $R^{4"}$, $R^{5"}$, $X_2"$, $X_3"$ and $X_4"$ are as defined above in formula (IB), and Prot is an amino protective group, such as described in T. W. Greene "Protective Groups in Organic Synthesis", Publishers John Wiley, 2nd edition 1991, the disclosure of which is specifically incorporated by reference herein, both protons of the amino protective group being protected, e.g. benzyl, paramethoxybenzyl or phthaloyl;

e) reacting a compound of the formula (XXXIV) or (XXXIV') after reaction of alkali metal hydrides, alkali metal carbonates or alkoxides in inert solvents, preferably DMF or NMP, followed by a treatment with $R^{6"}X$, where $R^{6"}$ is as defined above in formula (IB) and X is a leaving group, e.g. halogen, mesylate or tosylate, a compound of the formula (XXXV) or (XXXV') being obtained (XXXV)

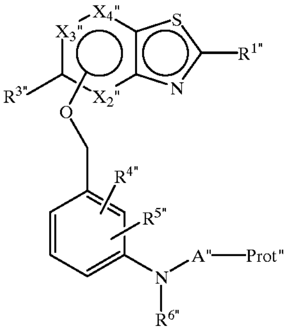

(XXXV')

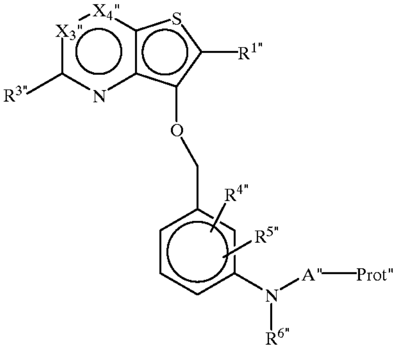

in which A", $R^{1"}$, $R^{3"}$, $R^{4"}$, $R^{5"}$, $R^{6"}$, $X_2^{41}$, $X_3$" and $X_4$" are as defined above in formula (IB) and Prot" is as defined above in formula (XXXIV);

f) for the removal of the protective group (Prot') from the compound of the formula (XXXV) or (XXXV'), in the case of the phthaloyl group preferably reacting with hydrazine in alcohols as solvents, at temperatures between room temperature and the boiling point, preferably at room temperature, a compound of the formula (XXXVI) or (XXXVI') being obtained (XXXVI)

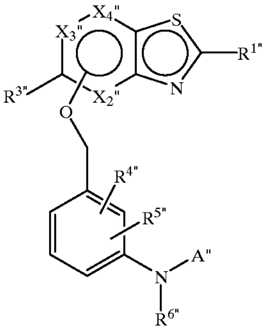

-continued (XXXVI')

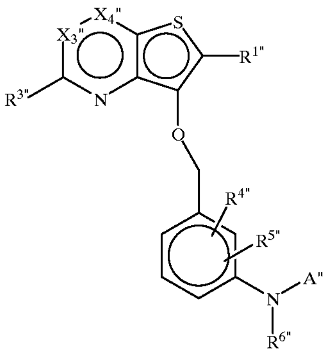

in which A", $R^{1"}$, $R^{3"}$, $R^{4"}$, $R^{5"}$, $R^{6"}$, $X_2$", $X_3$" and $X_4$" are as defined above in formula (IB) and Prot" is as defined above in formula (XXXIV);

$g_1$) reacting a compound of the formula (XXXVI) or (XXXVI') with activated acid derivatives of the formula (XXXVII), (XXXVIII) or (XXXIX)

E"-D"—C(O)—OH (XXXVII)

E"-D"—C(S)—OH (XXXVIII)

E"-D"—$SO_2$—OH (XXXIX)

in which D" and E" are as defined above in formula (XXII), preferably their acid chlorides, anhydrides or carboxylic acids of the formula (XXXVII), (XXXVIII) or (XXXIX), activated by reagents such as are used in peptide synthesis, or $g_2$) reacting a compound of the formula (XXXVI) or (XXXVI') with an amine or an alcohol of the formula (XL)

E"—D"—Z" (XL)

in which E" and D" are as defined above and Z is OH or $NH_2$, preferably at temperatures between 0° C. and room temperature in inert solvents, preferably dichloromethane or dimethoxyethane, first, however, the compounds of the formula (XXXV), (XXXV) or (XL) are allowed to react with a doubly activated carbonyl compound to form the urea or urethane group, e.g., with carbodiimides, phosgene or chlorocarbonic acid esters, preferably phosgene and carbonyldiimidazole, or $g_3$) reacting a compound of the formula (XXXVI) or (XXXVI') with an appropriate isocyanate or isothiocyanate, preferably at temperatures between 0° C. and room temperature in inert solvents, preferably dichloromethane or dimethoxyethane, and h) converting the compound of the formula (IB) obtained into its physiologically tolerable salts, if appropriate, according to known methods.

The replacement of chlorine by alkoxy or the corresponding S-alkyls is carried out by reaction with the appropriate alkoxides or thiolates, preferably their alkali metal or alkaline earth metal salts, in inert solvents, preferably DMF, NMP or the appropriate alcohol, at temperatures between 0° C. and 60° C., preferably between 0° C. and room temperature.

The replacement of chlorine by cyano is carried out by the action of cyanides, preferably the copper cyanides, in inert high-boiling solvents, such as, for example, DMF or NMP, at their boiling points.

For conversion to the bromoethyl compound, the coupling reagents and the coupling as such, and for the phthaloyl group, that carried out with the compounds of the formula (Ia) applies.

Particularly suitable compounds of the formula I are those in which:

D is 1) a radical of the formula (Xa)

(Xa)

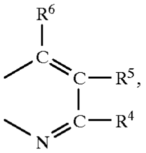

or 2) a radical of the formula (Xb)

(Xb)

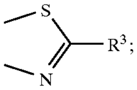

E is 1) a radical of the formula (XI)

(XI)

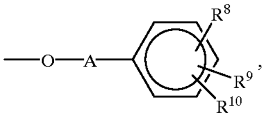

or 2) hydrogen, $(C_1–C_4)$-alkyl or $(C_1–C_4)$-alkoxy;

$R^1$ and $R^2$ are identical or different, and are hydrogen, halogen or $(C_1–C_4)$-alkyl;

$R^4$ is hydrogen, $(C_1–C_4)$-alkyl, phenyl or methoxy;

$R^5$ is 1) hydrogen, $(C_1–C_4)$-alkyl or

2)

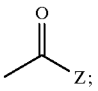

$R^6$ is 1) hydrogen, $(C_1–C_4)$-alkyl or 2) a radical of the formula (VIII)

(VIII)

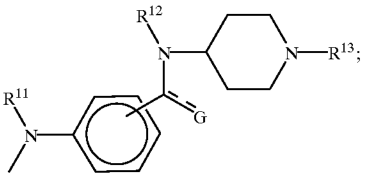

$R^8$ and $R^9$ are identical or different and are hydrogen, halogen, $(C_1–C_3)$-alkyl or $(C_1–C_3)$-alkoxy;

A is $—CH_2$- or $—CH_2–CH_2$-;

$R^{10}$ is a radical of the formula (IX):

(IX)

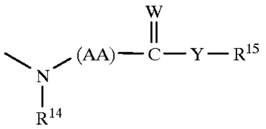

wherein W is oxo or sulfur;

$R^{11}$ is, identically or differently, hydrogen, methyl or ethyl;

$R^{14}$ is, identically or differently, hydrogen, methyl or ethyl;

G is oxo or 2 single-bonded hydrogen atoms;

$R^{12}$ is, if G is O, hydrogen, if G is 2 single-bonded hydrogen atoms, hydrogen or $R^{16}CO$;

$R^{13}$ is $(C_1–C_4)$-alkyl, cyclopentyl, cyclohexyl, $—(CH_2)_mCON(R^{11})_2$, or

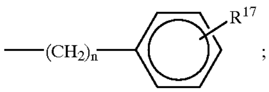

m and n are, identically or differently, a number from 0–2;

AA is the aminocarboxylic acid glycine or alanine;

Y is 1) $(C_2–C_4)$-alkenediyl,

2) $(C_2–C_4)$-alkanediyl,

3) $(C_3–C_6)$-cycloalkanediyl or

T is O or S;

o is a number 0 or 1;

p and q are identical or different, and are a number from 0–2;

$R^{15}$ is 1) hydrogen,

2) $(C_1–C_5)$-alkyl, 3) phenyl or

4) $(C_5–C_9)$-heteroaryl, where 3) and 4) can optionally be substituted by one, two or three identical or different groups, such as halogen, $NO_2$, $(C_1–C_3)$-alkylthio, $NR^{20}R^{21,}$ $NR^{20}CO—(C_1–C_5)$-alkyl and $NR^{20}CO$-pyridyl, $(C_1–C_3)$-alkyl or $(C_1–C_3)$-alkoxy, in which, if appropriate, the hydrogen atoms of the alkyl or alkoxy group can be partly or completely replaced by halogen;

$R^{16}$ is hydrogen, $(C_1–C_4)$-alkyl or phenyl;

$R^{17}$ is hydrogen, halogen, $(C_1–C_4)$-alkyl, $NO_2$ or , $NH_2$;

$R^{20}$ is independently hydrogen, $(C_1–C_4)$-alkyl or benzyl;

$R^{21}$ is independently hydrogen or $C(O)—O—(C_1–C_5)$-alkyl;

Z is $—N(R^{14})(R^{22})$;

$R^{22}$ is

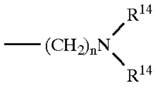

or

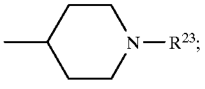

$R^{23}$ is $(C_1-C_4)$-alkyl,

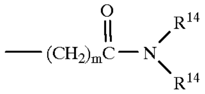

or

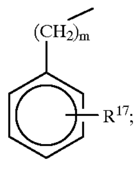

or a physiologically tolerable salt thereof.

Particularly suitable compounds of the formula (I) are those in which the symbols have the following meaning:

D is 1) a radical of the formula (Xa)

(Xa)

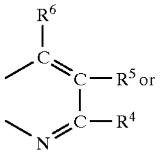

2) a radical of the formula (Xb)

(Xb)

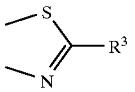

E is a radical of the formula (XI)

(XI)

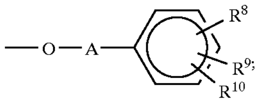

$R^1$ and $R^2$ are identical or different, and are hydrogen, halogen or $(C_1-C_4)$-alkyl;

$R^4$ is hydrogen or $(C_1-C_4)$-alkyl;

$R^5$ is hydrogen;

$R^6$ is hydrogen;

$R^8$ and $R^9$ are identical or different, and are hydrogen, chlorine, methyl or methoxy;

A is $—CH_2$- or $—CH_2–CH_2$-;

$R^{10}$ is a radical of the formula (IX)

(IX)

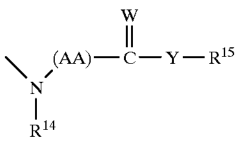

W is oxo;

$R^{14}$ is hydrogen, methyl or ethyl;

AA is the aminocarboxylic acid glycine;

Y is

1) $(C_2-C_5)$-alkenediyl,

2) $(C_2-C_4)$-alkanediyl,

3) $(C_3-C_6)$-cycloalkanediyl or

4) $—(CH_2)_p—T_o—(CH_2)_q$-;

T is O or S;

o is a number 0 or 1;

p and q are identical or different, and are a number from 0–2;

$R^{15}$ is 1) is hydrogen

2) $(C_1-C_3)$-alkyl, 3) phenyl or

4) $(C_5-C_9)$-heteroaryl, where 3) and 4) can optionally be substituted by one, two or three identical or different groups, such as halogen, $NO_2$, $NR^{20}R^{21}$, $NR^{20}CO—(C_1-C_3)$-alkyl and $NR^{20}CO$-pyridyl, $(C_{1-C_3})$-alkyl or $(C_1-C_3)$-alkoxy, in which, if appropriate, the hydrogen atoms of the alkyl or alkoxy group are partly or completely replaced by halogen;

$R^{20}$ is independently hydrogen, $(C_1-C_4)$-alkyl or benzyl;

$R^{21}$ is hydrogen or C(O)—O—$(C_1$–C,)-alkyl;

or a physiologically tolerable salt thereof.

Very particularly suitable compounds are:

N-{1-{4-(1,1-dimethylethyl)phenyl}methyl-4-piperidinyl}-8-methoxy-4-{{4-{{{1-(phenylmethyl)-4-piperidinyl}amino}carbonyl}phenylamino}-3-quinolinecarboxamide;

N-{1-{(3-chlorophenyl}methyl4-piperidinyl}-8-methoxy-4-{{4-{{{1-(phenylmethyl)-4-piperidinyl}amino}carbonyl}phenylamino}-3-quinolinecarboxamide;

8-methoxy-N-{1-(phenyl}methyl-4-piperidinyl-{4-{{4-{{{1-(phenylmethyl)4-piperidinyl}amino}carbonyl}phenylamino}-3-quinolinecarboxamide;

N-{2-(dimethylamino)ethyl}8-methoxy-4-(4-{{{1-(phenylmethyl)-4-piperidinyl}amino}carbonyl}phenyl-amino}3-quinoline carboxamide trifluoroacetate;

N-{2-(dimethylamino)ethyl}-N-ethyl-8-methoxy-4{{4-{{{1-(phenylmethyl)-4-piperidinyl}amino}carbonyl}phenylamino}-3-quinolinecarboxamide;

4-{{4-{{{(3-cyclopentyl-1 -oxopropyl)1{-{6-(diethylamino)-6-oxo-hexyl4-piperidinylamino}methyl-phenyl}amino-8-methoxy-N-{1-(phenylmethyl)4-piperidinyl}-3-quinolinecarboxamide;

4-{{44-{{(1-butyl-4-piperidinylamino}methyl}phenylamino}-8-methoxy-N-{1-(phenylmethyl)-4-piperidinyl}-3-quinolinecarboxamide;

N-(1 -butyl4-piperidinyl)-8-methoxy-{{4-{{{1-(phenylmethyl)-4-piperidinyl}amino}carbonyl}phenyl}amino}-3-quinolinecarboxamide;

N-{1-{6-(diethylamino)-6-oxohexyl4-piperidinyl-8-methoxy-4-{{4-{{{1-(phenylmethyl)-4-piperidinyl}amino}carbonyl}phenyl}amino}-3-quinolinecarboxamide;

4-{{4-{{(1 -butyl-4-piperidinyl)-(1-oxobutyl)amino}methyl}phenyl}amino-{8-methoxy-N-{1-(phenylmethyl)-4-piperidinyl}-3-quinolinecarboxamide;

N-{1-{4-(diethylamino)carbonylphenyl4-piperidinyl-8-methoxy-4-{{4-{{{1-(phenylmethyl)-4-piperidinyl}amino}carbonyl}phenyl}amino-3-quinolinecarboxamide;

N-{1-(2-phenylethyl)-4-piperidinyl}-8-methoxy-4-{{4-{{{1-(phenylmethyl)-4-piperidinyl}amino}carbonyl}phenyl}amino}-3-quinolinecarboxamide;

4-{{4-{{(1 -butyl-4-piperidinyl)amino}carbonyl}phenyl}amino}-8-methoxy-N-{1-(phenylmethyl)-4-piperidinyl-3-quinolinecarboxamide;

8-methoxy-N-(1-methyl4-piperidinyl)-4-{{4-{{{1-(phenylmethyl)-4-piperidinyl}amino}carbonyl}phenyl}amino}-3-quinolinecarboxamide;

N-{1-{{3-methoxyphenyl)methyl}-4-piperidinyl-8-methoxy-4-{{4-{{{1-(phenylmethyl)4-piperidinyl}amino}carbonyl}phenyl}amino-3-quinolinecarboxamide;

8-methoxy-4-{{4-{{{1-(phenylmethyl)-4-piperidinyl}amino}carbonyl}phenyl}-amino}-1-{{3-(trifluoromethyl)phenyl}methyl}-4-piperidinyl}-3-quinolinecarboxamide;

7-chloro-N-{1-(phenylmethyl)-4-piperidinyl}-4-{{4-{{{1-(phenylmethyl)-4-piperidinyl}amino}carbonyl}phenyl}amino}-3-quinolinecarboxamide; or a physiologically tolerable salt thereof. Very particularly suitable are the following compounds of Examples 1 to 118, which are listed in Tables 1 to 10.

TABLE 1

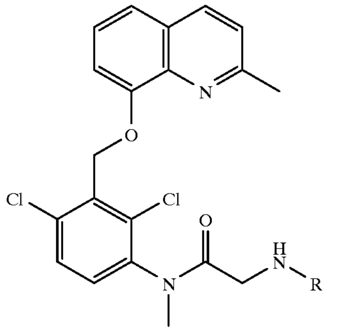

| Example | R |
|---|---|
| 1 | 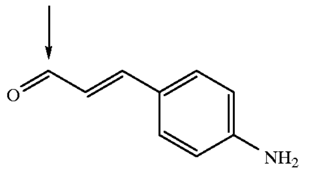 |
| 2 | 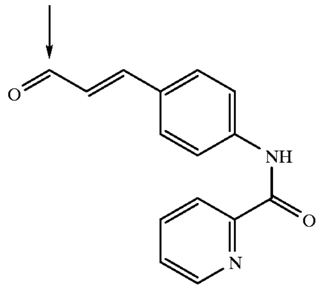 |
| 3 | 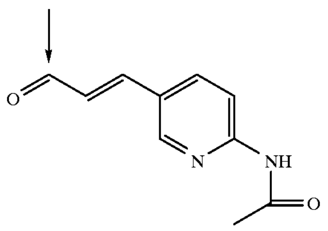 |

TABLE 1-continued

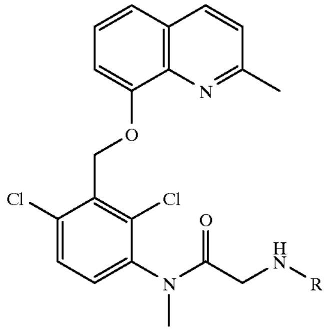

| Example | R |
|---|---|
| 4 | 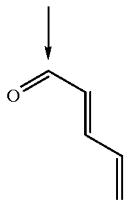 |
| 5 | 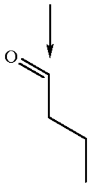 |
| 6 | 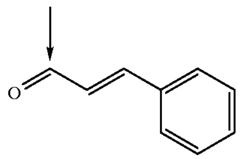 |
| 7 | 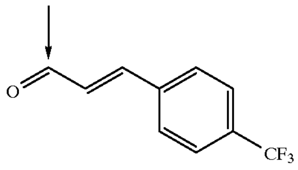 |
| 8 | 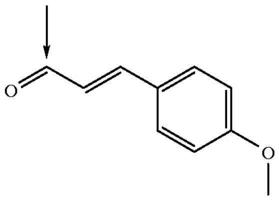 |

TABLE 1-continued
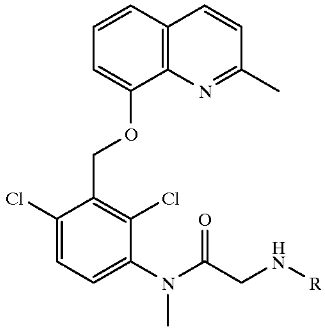
| Example | R |
| --- | --- |
| 9 | 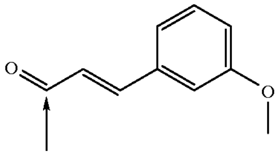 |
| 10 | 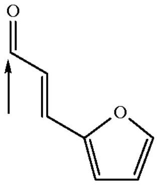 |
| 11 | 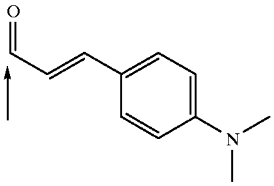 |
| 12 | 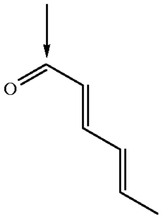 |
| 13 | 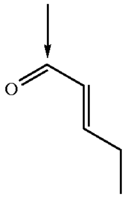 |
TABLE 1-continued
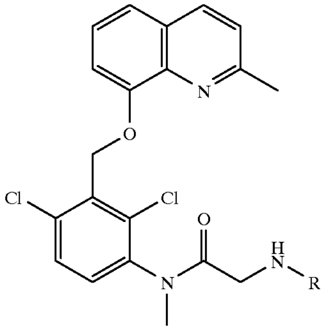
| Example | R |
| --- | --- |
| 14 | 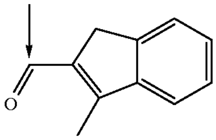 |
| 15 | 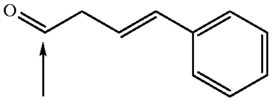 |
| 16 | 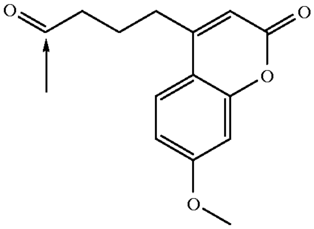 |
| 17 | 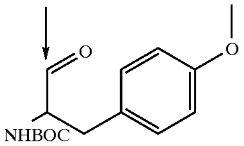 |
| 18 | 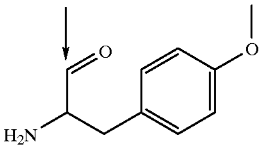 |
| 19 | 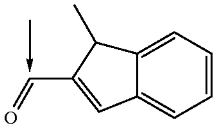 |

TABLE 1-continued
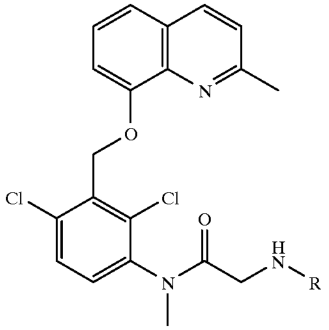
| Example | R |
|---|---|
| 20 | 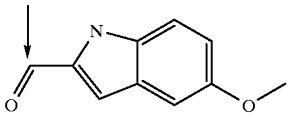 |
| 21 | 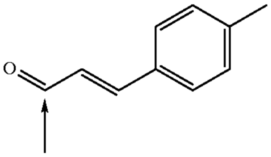 |
| 22 | 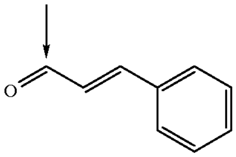 |
| 23 | 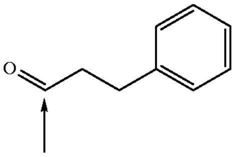 |
| 24 | 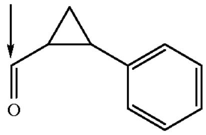 |
| 25 | 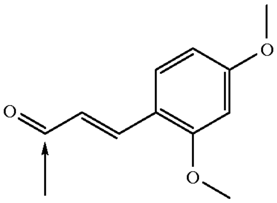 |
TABLE 1-continued
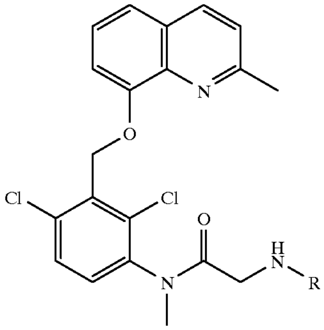
| Example | R |
|---|---|
| 26 | 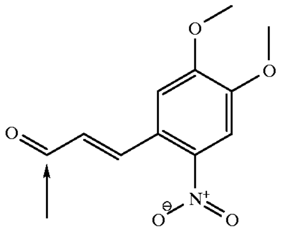 |
| 27 | 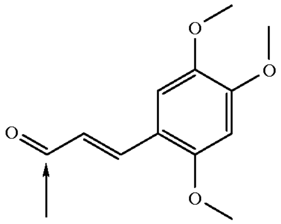 |
| 28 | 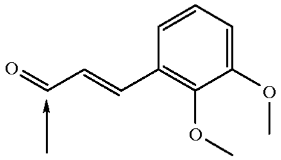 |
| 29 | 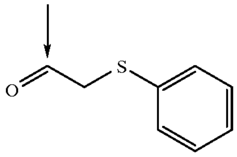 |
| 30 | 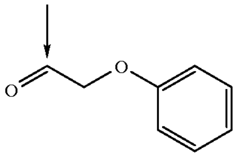 |

TABLE 1-continued
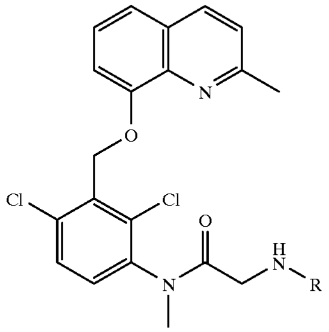
| Example | R |
| --- | --- |
| 31 | 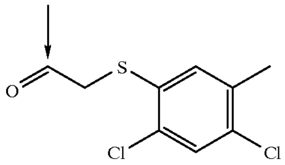 |
| 32 | 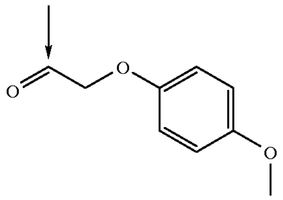 |
| 33 | 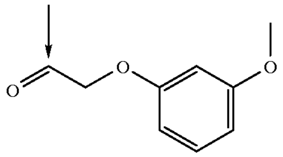 |
| 34 | 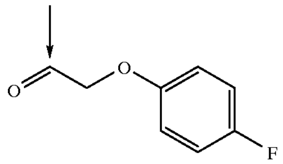 |
TABLE 2
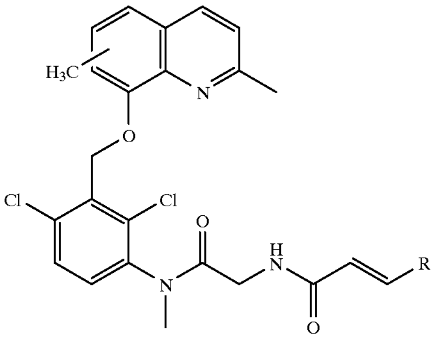
| Example | R | Pos-$CH_3$ |
| --- | --- | --- |
| 35 | 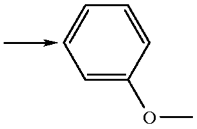 | 6 |
| 36 | 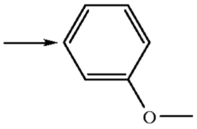 | 5 |
| 37 | 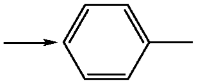 | 5 |
| 38 | 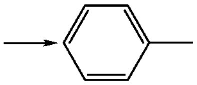 | 6 |
| 39 | 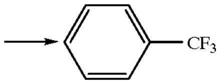 | 5 |
| 40 | 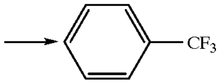 | 6 |

TABLE 3
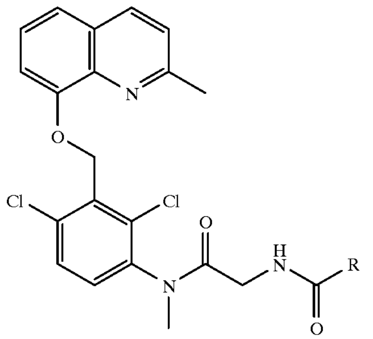
| Example | R |
|---|---|
| 41 | 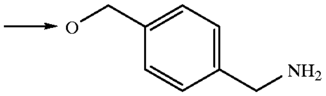 |
| 42 | 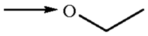 |
| 43 | 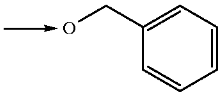 |
| 44 | 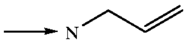 |
| 45 | 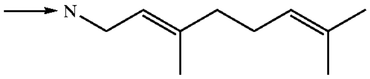 |
TABLE 4
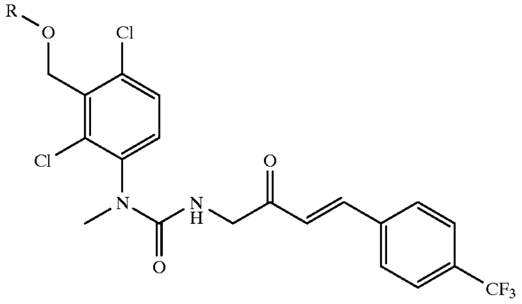
| Exam-ple | R |
|---|---|
| 46 | 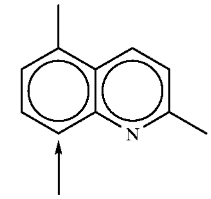 |
| 47 | 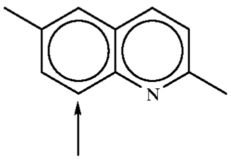 |
| 48 | 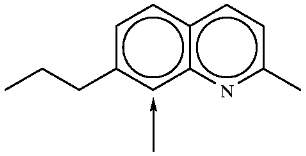 |
| 49 | 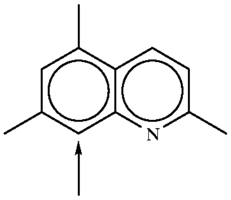 |

TABLE 5
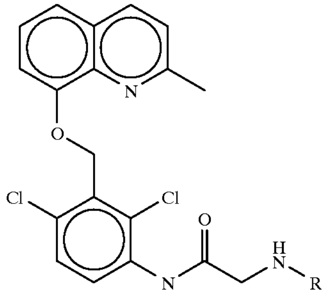
| Example | R |
|---|---|
| 50 | 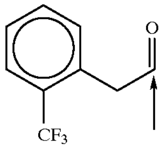 |
| 51 | 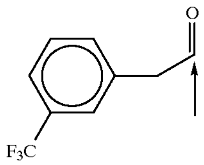 |
| 52 | 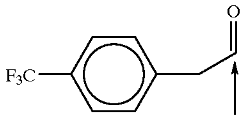 |
| 53 | 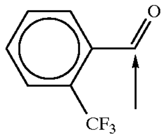 |
| 54 | 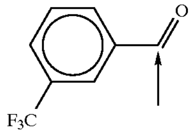 |
| 55 | 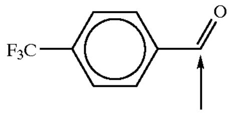 |
| 56 | 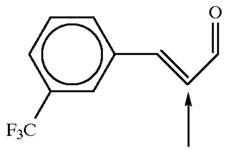 |
TABLE 5-continued
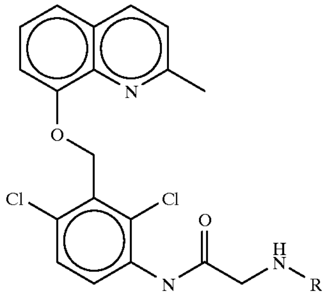
| Example | R |
|---|---|
| 57 | 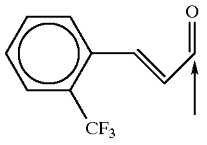 |
TABLE 6
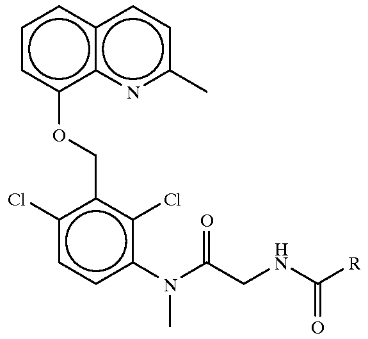
| Example | R |
|---|---|
| 58 | 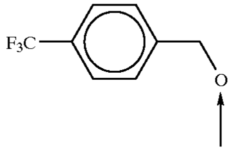 |
| 59 | 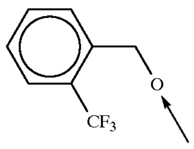 |
| 60 | 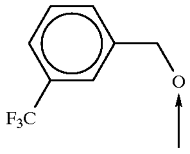 |

TABLE 6-continued
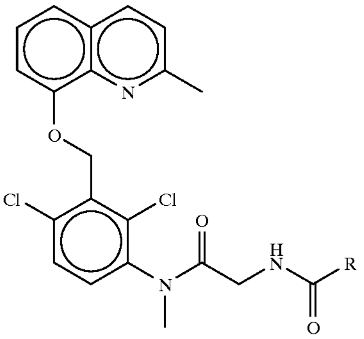
| Example | R |
|---|---|
| 61 | 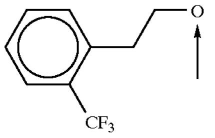 |
| 62 | 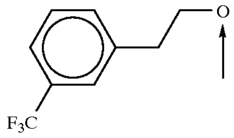 |
| 63 | 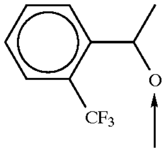 |
| 64 | 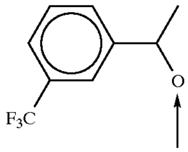 |
| 65 | 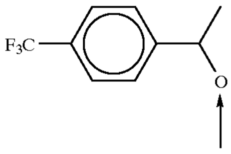 |
| 66 | 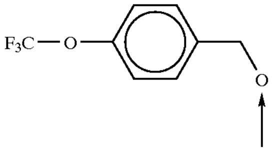 |
TABLE 6-continued
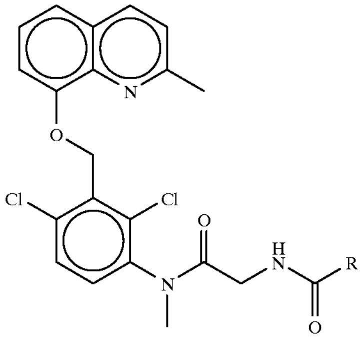
| Example | R |
|---|---|
| 67 | 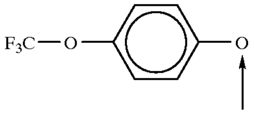 |
| 68 | 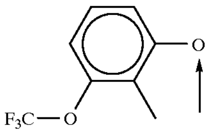 |
TABLE 7
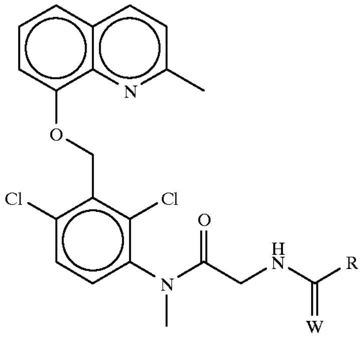
| Example | R | W |
|---|---|---|
| 69 | 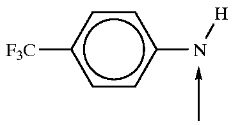 | O |
| 70 | 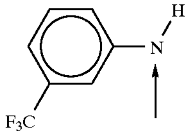 | O |

TABLE 7-continued
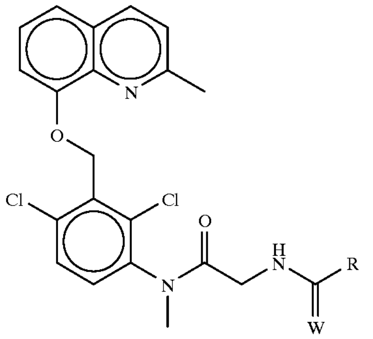
| Example | R | W |
|---|---|---|
| 71 | 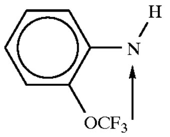 | O |
| 72 | 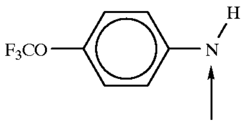 | O |
| 73 | 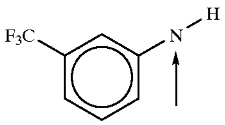 | O |
TABLE 8
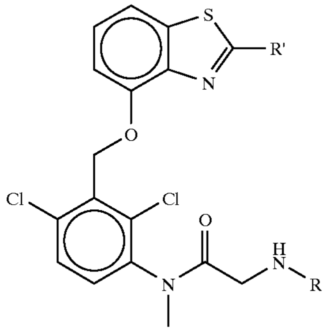
| Example | R | R' |
|---|---|---|
| 74 | 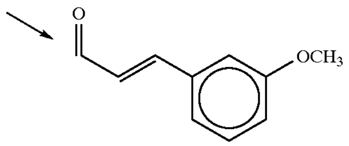 | H |
TABLE 8-continued
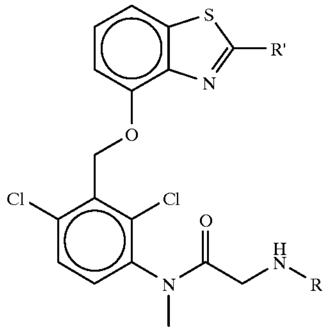
| Example | R | R' |
|---|---|---|
| 75 | 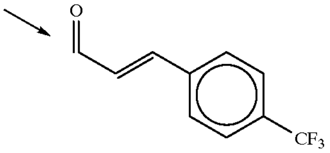 | $CH_3$ |
| 76 | 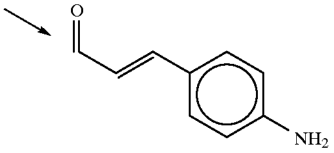 | $CH_3$ |
| 77 | 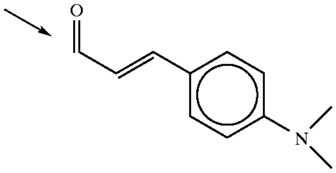 | $CH_3$ |
| 78 | 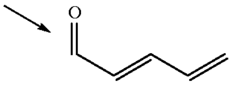 | $CH_3$ |
| 79 | 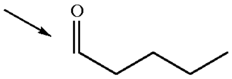 | $CH_3$ |
| 80 | 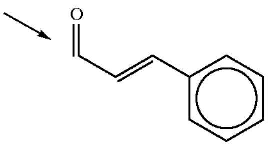 | $CH_3$ |
| 81 | 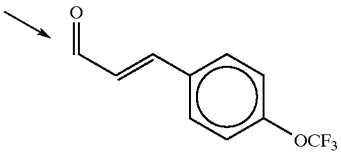 | $CH_3$ |

TABLE 8-continued
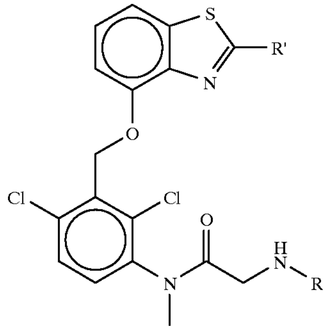
| Example | R | R' |
|---|---|---|
| 82 | 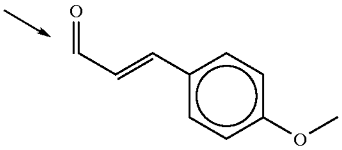 | $CH_3$ |
| 83 | 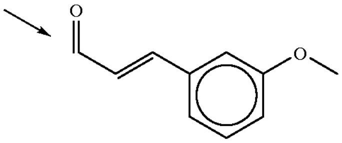 | $CH_3$ |
| 84 | 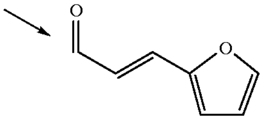 | $CH_3$ |
| 85 | 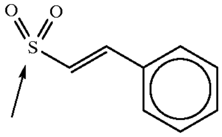 | $CH_3$ |
| 86 | 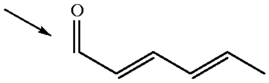 | $CH_3$ |
| 87 | 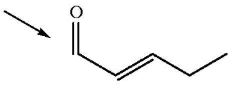 | $CH_3$ |
| 88 | 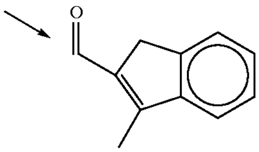 | $CH_3$ |
TABLE 8-continued
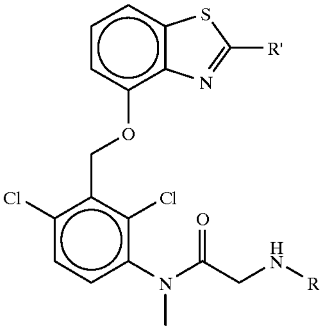
| Example | R | R' |
|---|---|---|
| 89 | 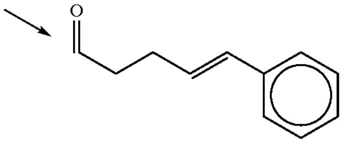 | $CH_3$ |
| 90 | 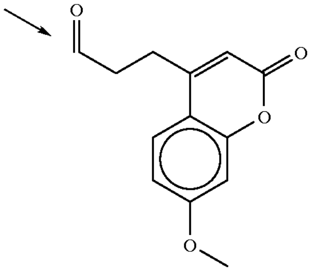 | $CH_3$ |
| 91 | 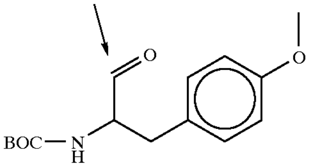 | $CH_3$ |
| 92 | 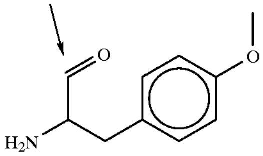 | $CH_3$ |
| 93 | 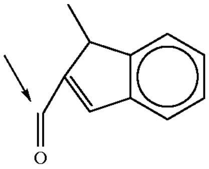 | $CH_3$ |

TABLE 8-continued
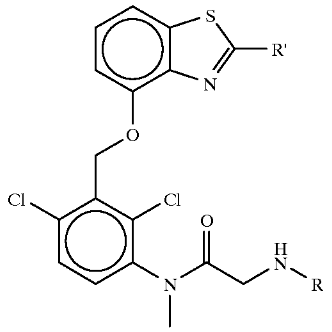
| Example | R | R' |
|---|---|---|
| 94 | 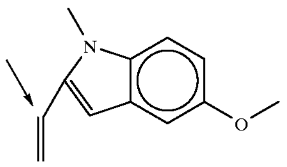 | $CH_3$ |
| 95 | 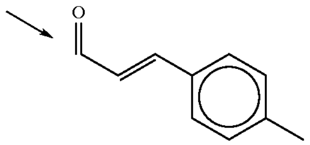 | $CH_3$ |
| 96 | 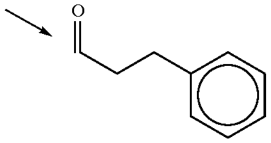 | $CH_3$ |
| 97 | 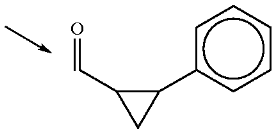 | $CH_3$ |
| 98 | 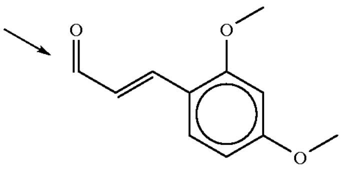 | $CH_3$ |
| 99 | 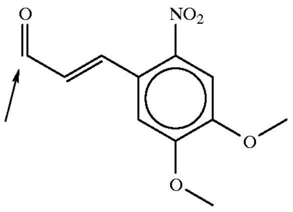 | $CH_3$ |
TABLE 8-continued
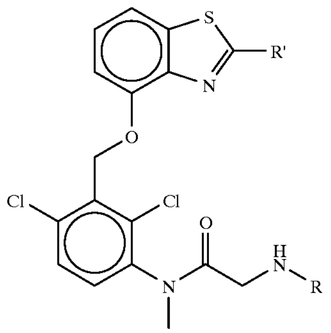
| Example | R | R' |
|---|---|---|
| 100 | 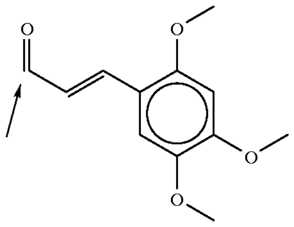 | $CH_3$ |
| 101 | 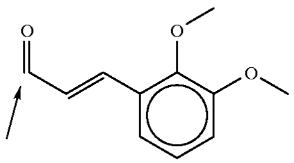 | $CH_3$ |
| 102 | 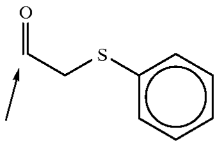 | $CH_3$ |
| 103 | 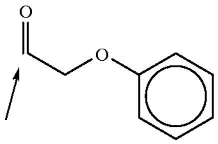 | $CH_3$ |
| 104 | 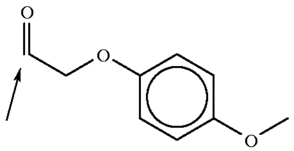 | $CH_3$ |
| 105 | 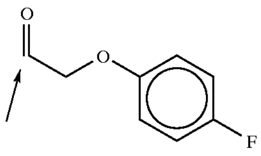 | $CH_3$ |

TABLE 8-continued

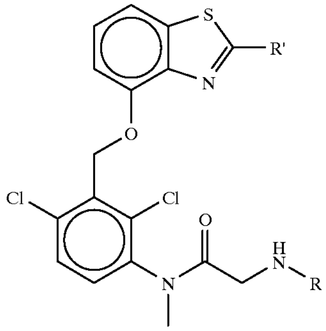

| Example | R | R' |
|---|---|---|
| 106 | 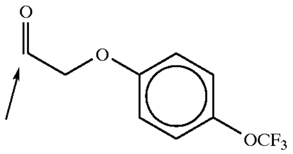 | $CH_3$ |
| 107 | 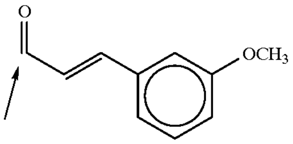 | $CH_3$ |
| 108 | 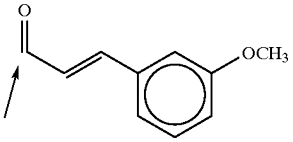 | 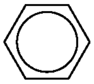 |
| 109 | 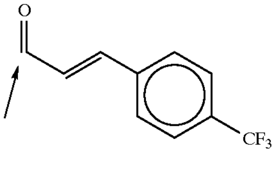 | 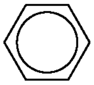 |
| 110 | 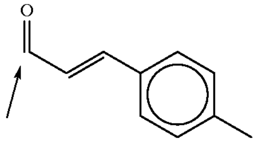 | 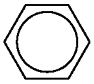 |

TABLE 9

| Example | R | R" |
|---|---|---|
| 111 | 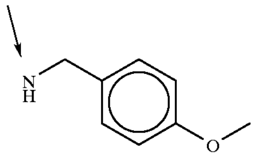 | $CH_3$ |
| 112 | 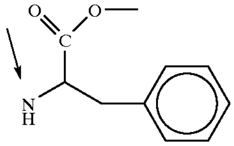 | $CH_3$ |
| 113 | 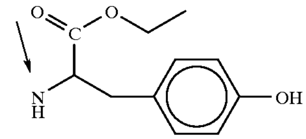 | $CH_3$ |
| 114 | 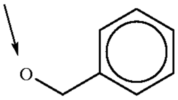 | $CH_3$ |

TABLE 10

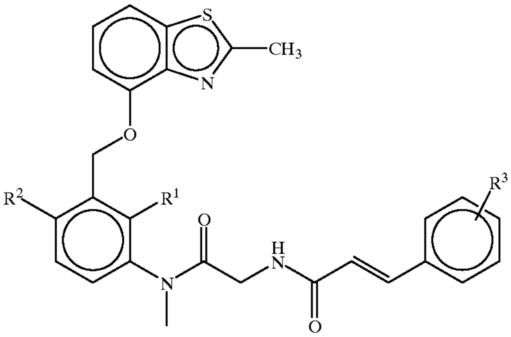

| Example | $R^1$ | $R^2$ | $R^3$ |
|---|---|---|---|
| 115 | Cl | $OCH_3$ | 4-$CF_3$ |
| 116 | $OCH_3$ | Cl | 4-$CF_3$ |
| 117 | $OCH_3$ | $OCH_3$ | 4-$CF_3$ |

Administration can be carried out enterally, parenterally, such as, for example, subcutaneously, i.m. or i.v., nasally, rectally or by inhalation. The dose of the active compound depends on the body weight, age and on the manner of administration.

The pharmaceutical preparations of the present invention are prepared in a dissolving, mixing, granulating, tableting or sugar-coating process known per se.

For parenteral administration, the active compounds or their physiologically tolerable salts are brought into solution, suspension or emulsion, if desired using the pharmaceutically customary auxiliaries, for example for isotonicization or pH adjustment, and also solubilizers, emulsifiers or other auxiliaries.

For the pharmaceuticals described, the use of injectable delayed release preparation is also useful for subcutaneous or intramuscular administration. It is possible to use as pharmaceuticals, for example, oily crystal suspensions, microcapsules, microparticles, nanoparticles or implants, it being possible to construct the latter from tissue-tolerable polymers, in particular biodegradeable polymers, e.g. on the basis of polylactic acid/polyglycolic acid copolymers. Other possible polymers are polyamides, polyesters, polyacetates or polysaccharides.

For the oral administration form, the active compounds are mixed with the additives customary for this such as excipients, stabilizers or inert diluents, and brought by customary methods into suitable administration forms, such as tablets, coated tablets, dry-filled capsules, aqueous alcoholic or oily suspensions or aqueous alcoholic or oily solutions. It is possible to use as inert excipients, for example, gum arabic, magnesia, magnesium carbonate, potassium phosphate, lactose, glucose, magnesium stearyl fumarate or starch, in particular corn starch. In this case, the preparation of solid pharmaceuticals can take place both as dry and moist granules. Suitable oily excipients or solvents are, for example, vegetable or animal oils, such as sunflower oil and cod liver oil.

Oral delayed release preparations or preparations with enteric coatings are also possible. Delayed release preparations can be based on fat, wax or polymer embeddings. Multilayer or press-coated tablets or pellets are also possible here.

For the pharmaceuticals described, administration to mucous membranes to achieve systemically active levels is also useful. This relates to the possibility of administration intranasally, by inhalation and rectally.

For the intranasal administration form, the compounds are mixed with the additives customary for this, such as stabilizers or inert diluents; and brought by customary methods into suitable administration forms, such as powders, aqueous alcoholic or oily suspensions or aqueous, alcoholic or oily solutions. Chelating agents, such as ethylene diamine-N,N,N',N'-tetracetic acid and buffers such as acetic acid, phosphoric acid, citric acid, tartaric acid and their salts can be added to aqueous intranasal preparations. Multiple dose containers contain preservatives such as benzalkonium chloride, chlorobutanol, chlorhexidine, sorbic acid, benzoic acid, PHB esters or organomercury compounds.

The nasal solutions can be administered by means of metering atomizers or as nasal drops with a viscosity-increasing component or nasal gels or nasal creams.

For administration by inhalation, atomizers or pressurized gas packs using inert carrier gases can be used.

For the administration of powders for nasal or pulmonary inhalation, special applicators are necessary.

In practicing the method according to the invention, the non-peptide bradykinin antagonists described above can be administered to mammals such as humans, apes, dogs, cats, rats etc.

The effective dose of the compounds of the formula (I) is at least 0.01 mg/kg/day, preferably at least 0.1 mg/kg/day, at most 30 mg/kg/day, preferably 0.3 to 10 mg/kg/day of body weight, depending on the degree of severity of the symptoms, based on an adult of body weight 75 kg.

EXAMPLE 1

Action of the compounds of the formula (I) on the cGMP production stimulated by the Alzheimer protein β/A4 in endothelial cell cultures Test systems:

Bovine aortic endothelial cell cultures (BAECs=bovine aortic endothelial cells), intravascular coronary rat endothelial cultures (RMCECs=rat microvascular coronary endothelial cells) and human umbilical cord endothelial cell cultures (HUVECs=human umbilical vein endothelial cells)

Method:

Determination of the effects of bradykinin antagonists of the formula (I) on the production of cGMP stimulated by administration of 0.1 and 1 μmol/l of the Alzheimer's{-}protein β/A4 in endothelial cell cultures of various species and organs.

cGMP: cyclic guanosine monophosphate

It has adequately been shown that endothelial cells are a suitable test system for the demonstration of an action and release of bradykinin (G. Wiemer et al., Hypertension 1991; 18: 558–563). In endothelial cells, bradykinin leads to an increase in the production of cGMP, which is determined by means of a radioimmunoassay. Increase in the formation of cGMP by bradykinin is an indicator of a release of NO (nitrogen monoxide) from endothelial cells.

Experiment:

Stimulation of cGMP production by βA (1–40) and inhibitory effects of the bradykinin antagonists of Examples 3 and 7 ($10^{-7}$ mol/l) in 3 different types of endothelial cells:

| Endothelial cell type: | BAECs conc. cGMP | RMCECs (pmol/mg | HUVECs of protein) |
|---|---|---|---|
| Basal cGMP-Production | 2.2 ± 0.35 | 0.2 ± 0.07 | 4.75 ± 0.4 |
| BK $10^{-8}$ mol/l 8.8 ± 0.34 | 1.13 ± 0.2 | 11.46 ± 2 | |
| BK $10^{-8}$ mol/l + Example 7 | 1.9 ± 0.19 | 0.30 ± 0.03 | 4.02 ± 0.45 |
| βA (1–40) $10^{-7}$ mol/l | 5.9 ± 0.23 | 0.59 ± 0.07 | 14.07 ± 1.6 |
| βA (1–40) $10^{-7}$ mol/l + Ex. 7 | 1.0 ± 0.1 | 0.24 ± 0.01 | 4.26 ± 0.45 |
| βA (1–40) $10^{-6}$ mol/l | 4.6 ± 0.13 | 0.74 ± 0.09 | 15.3 ± 1.9 |
| βA (1–40) $10^{-6}$ mol/l + Ex. 7 | 3.0 ± 0.14 | 0.39 ± 0.03 | 5.9 ± 0.55 |
| βA (1–40) $10^{-6}$ mol/l + Ex. 3 | 1.9 ± 0.14 | 0.30 ± 0.04 | 4.2 ± 0.43 |

Results:

The simultaneous incubation of the abovementioned cell cultures of different species and organs with compounds of Examples 3 and 7 as representative examples of the compounds of the formula (I) in a concentration of 0.1 μmol/l prevents the stimulation of the production of cGMP caused by β/4A protein.

Assessment

The experiment carried out indicates that the action of the Alzheimer protein β/A4 on the production of cGMP is mediated via a binding of bradykinin to its cell receptors. Endothelial cell cultures are used here as an indicator that the action of β/A4 is mediated by bradykinin. The endothelial cells here, however, are not only the indicator system for an action on bradykinin receptors, but also the effector organ in Alzheimer's disease. Endothelial cells are constituents of the blood vessels and form these. The blood vessels themselves are severely affected by deposits of the Alzheimer's protein amyloid (β/A4) in Alzheimer's disease in addition to neuronal tissue. Endothelial cells are responsible for an increase in the permeability of the blood-brain barrier caused by bradykinin.

We claim:

1. A method for the treatment or prevention of Alzheimer's disease comprising the step of administering to a host in recognized need of such treatment an amount of a non-peptide bradykinin antagonist, or a physiologically tolerable salt thereof, effective to achieve said treatment.

2. The method as claimed in claim 1, wherein said non-peptide bradykinin antagonist is a compound of the formula (I):

(I)

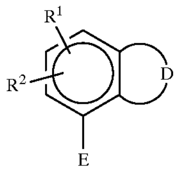

in which the symbols have the following meanings:

D is 1) a radical of the formula (II)

(II)

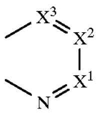

or 2) a radical of the formulae (III) to (VI)

(III)

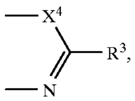

(IV)

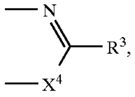

(V)

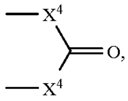

and (VI)

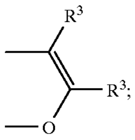

E is 1) a radical of the formula (VII)

(VII)

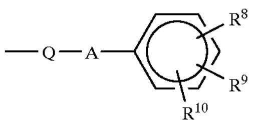

or 2) hydrogen, halogen, ($C_1$–$C_4$)-alkyl, ($C_1$–$C_4$)-alkylthio or ($C_1$–$C_4$)-alkoxy, where in the last 3 radicals 1 or more hydrogen atoms can be replaced by fluorine;

$X^1$ is nitrogen or C—$R^4$;

$X^2$ is nitrogen or C—$R^5$;

$X^3$ is nitrogen or C—$R^6$;

$X^4$ is independently oxygen, sulfur, nitrogen or N—$R^7$;

$R^1$ and $R^2$ are identical or different and are hydrogen, halogen, ($C_1$–$C_4$)-alkyl or ($C_1$–$C_4$)-alkoxy;

$R^3$ is independently hydrogen, halogen, ($C_1$–$C_6$)-alkyl, ($C_6$–$C_{12}$)-aryl, ($C_1$–$C_3$)-alkyl-($C_6$–$C_{12}$)-aryl, ($C_1$–$C_5$)-alkenyl, ($C_1$–$C_4$)-alkoxy or $CO_2R^{11}$;

$R^4$ is hydrogen, halogen, ($C_1$–$C_4$)-alkyl, hydroxyl, ( $C_1$–$C_4$)-alkylthio, amino, ($C_1$–$C_4$)-alkylamino, ($C_1$–$C_4$)-dialkylamino, ($C_1$–$C_4$)-alkoxy, in which the alkyl part of any of the preceding substituents is optionally substituted by hydroxyl, ($C_1$–$C_4$)-alkoxy, amino and ($C_1$–$C_4$)-alkylamino, or ($C_6$–$C_{12}$)-aryl, optionally substituted by ($C_1$–$C_4$)-alkyl or $CO_2R^{11}$;

$R^5$ is 1) hydrogen, ($C_1$–$C_4$)-alkyl or

2)

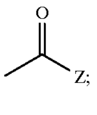

$R^6$ is 1) hydrogen, halogen, ($C_1$–$C_4$)-alkyl, hydroxyl, ($C_1$–$C_4$)-alkylthio, amino, ($C_1$–$C_4$)-alkylamino, ($C_1$–$C_4$)-dialkylamino, ($C_1$–$C_4$)-alkoxy, in which the alkyl part of any of the preceding substituents is optionally substituted by hydroxyl, ($C_1$–$C_4$)-alkoxy, amino and ($C_1$–$C_4$)-alkylamino, or ($C_6$–$C_{12}$)-aryl, optionally substituted by ($C_1$–$C_4$)-alkyl or $CO_2R^{11}$; or 2) a radical of the formula (VIII)

(VIII)

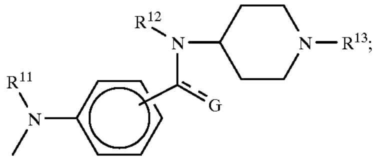

$R^7$ is independently ($C_1$–$C_4$)-alkyl, ($C_6$–$C_{12}$)-aryl or ($C_1$–$C_3$)-alkyl-($C_6$–$C_{12}$)-aryl;

$R^8$ and $R^9$ are identical or different and are hydrogen, halogen, ($C_1$–$C_3$)-alkyl or ($C_1$–$C_3$)-alkoxy;

A is ($C_1$–$C_3$)-alkanediyl;

Q is O or $NR^{11}$;

$R^{10}$ is a radical of the formula (IX)

(IX)

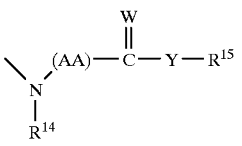

wherein W is oxo or sulfur;

$R^{11}$ is independently hydrogen or ($C_1$–$C_4$)-alkyl;

$R^{14}$ is independently hydrogen or ($C_1$–$C_4$)-alkyl;

G is oxo or 2 single-bonded hydrogen atoms;

$R^{12}$ is, if G is oxo, hydrogen and if G is 2 single-bonded hydrogen atoms, hydrogen or $R^{16}CO$;

$R^{13}$ is ($C_1$–$C_4$)-alkyl, ($C_3$–$C_7$)-cycloalkyl, —$(CH_2)_m$-($C_3$–$C_7$)-cycloalkyl, —$(CH_2)_m$-$CON(R^{11})_2$, or

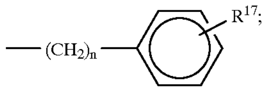

m and n are, identically or differently, a number from 0–6;

AA is an amino acid such as methionine, alanine, phenylalanine, 2-chlorophenylalanine, 3-chlorophenylalanine, 4-chlorophenyl-alanine, 2-fluorophenylalanine, 3-fluorophenylalanine, 4-fluorophenylalanine, tyrosine, o-methyltyrosine, β-(2-thienyl)-alanine, glycine, cyclohexylalanine, leucine, isoleucine, valine, norleucine, phenylglycine, serine, cysteine, aminopropionic acid or aminobutyric acid;

Y is 1) ($C_2$–$C_5$)-alkenediyl, 2) ($C_1$–$C_8$)-alkanediyl, 3) ($C_3$–$C_{10}$)-cycloalkanediyl or 4) $-(CH_2)_p-T_o-(CH_2)_q-$, where 1) to 4) can optionally be substituted by one or more identical or different radicals such as O—$R^8$, $NO_2$, CN, $CO_2R^{11}$, $SO_3R^{18}$, $NR^{20}R^{21}$, $SO_2NR^{20}R^{21}$, $CONR^{20}R^{21}$;

T is O, $NR^{21}$ or S;

o is a number O or 1;

p and q are identical or different and denote a number from 0 to 6;

$R^{15}$ independently is 1) hydrogen, 2) ($C_1$–$C_5$)-alkyl, 3) ($C_6$–$C_{10}$)-aryl or 4) ($C_1$–$C_9$)-heteroaryl, where 3) and 4) can optionally be substituted by one or more identical or different groups, such as halogen, CN, $NO_2$, ($C_1$–$C_5$)-alkylthio, $NR^{20}R^{21}$, $CO_2R^{19}$, $SO_3R^{18}$, $SO_2NR^{20}R^{21}$, $SO_2R^{18}$, O—$R^{18}$, $NR^{20}CO$—$R^{15}$, ($C_1$–$C_6$)-alkyl, ($C_6$–$C_{10}$)-aryl, ($C_2$–$C_5$)-alkenyl or ($C_1$–$C_5$)-alkoxy, where the last four radicals can optionally be partly or completely substituted by halogen;

$R^{16}$ is independently hydrogen, ($C_1$–$C_4$)-alkyl, ($C_6$–$C_{12}$)-aryl, ($C_1$–$C_4$)-alkyl-($C_6$–$C_{12}$)-aryl or perfluoro-($C_1$–$C_4$)-alkyl;

$R^{17}$ is hydrogen, halogen, ($C_1$–$C_4$)-alkyl, ($C_1$–$C_4$)-alkoxy, perfluoro-($C_1$–$C_4$)-alkyl, $NO_2$, OH, $NH_2$, $CON(R^{16})_2$ or $NR^{16}CON(R^{16})_2$;

$R^{18}$, $R^{19}$ and $R^{20}$ are each identical or different and are hydrogen, ($C_1$–$C_5$)-alkyl, ($C_3$–$C_5$)-alkenyl, ($C_6$–$C_{12}$)-aryl-($C_1$–$C_3$)-alkyl, ($C_3$–$C_{10}$)-cycloalkyl, ($C_3$–$C_{10}$)-cycloalkyl-($C_1$–$C_3$)-alkyl, C(O)—O—($C_1$–$C_5$)-alkyl or C(O)—NH—($C_1$–$C_5$)-alkyl;

$R^{21}$ is independently hydrogen, C(O)—O—($C_1$–$C_5$)-alkyl or C(O)—O—($C_1$–$C_3$)-alkyl-($C_6$–$C_{10}$)-aryl;

Z is —N(R:$^{14}$)($R^{22}$);

$R^{22}$ is

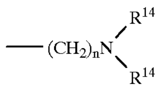 or 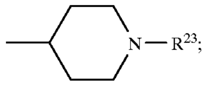

$R^{23}$ is ($C_1$–$C_4$)-alkyl,

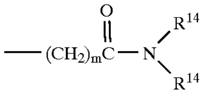 or 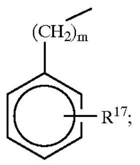

or a physiologically tolerable salt thereof.

3. The method as claimed in claim 2, in which said non-peptide bradykinin antagonist of the formula (I), wherein:

D is 1) a radical of the formula (Xa)

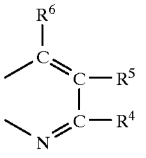

2) a radical of the formula (Xb)

(Xb)

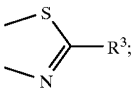

E is 1) a radical of the formula (XI)

(XI)

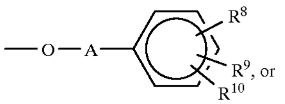

2) hydrogen, ($C_1$–$C_4$)-alkyl or ($C_1$–$C_4$)-alkoxy;

$R^1$ and $R^2$ are identical or different, and are hydrogen, halogen or ($C_1$–$C_4$)-alkyl;

$R^4$ is hydrogen, ($C_1$–$C_4$)-alkyl, phenyl or methoxy;

$R^5$ is 1) hydrogen, ($C_1$–$C_4$)-alkyl or

2)

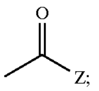

$R^6$ is 1) hydrogen, ($C_1$–$C_4$)-alkyl or 2) a radical of the formula (VIII)

(VIII)

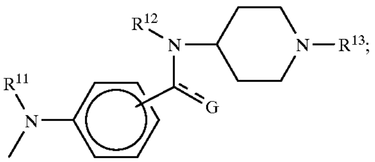

$R^8$ and $R^9$ are identical or different and are hydrogen, halogen, $(C_1-C_3)$-alkyl or $(C_1-C_3)$-alkoxy;

A is $-CH_2-$ or $-CH_2-CH_2-$;

$R^{10}$ is a radical of the formula (IX):

(IX)

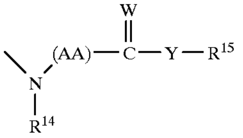

wherein W is oxo or sulfur;

$R^{11}$ is, identically or differently, hydrogen, methyl or ethyl;

$R^{14}$ is, identically or differently, hydrogen, methyl or ethyl;

G is oxo or 2 single-bonded hydrogen atoms;

$R^{12}$ is, if G is O, hydrogen and if G is 2 single-bonded hydrogen atoms, hydrogen or $R^{16}CO$;

$R^{13}$ is $(C_1-C_4)$-alkyl, cyclopentyl, cyclohexyl, $-(CH_2)_mCON(R^{11})_2$, or

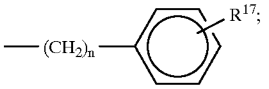

m and n are, identically or differently, a number from 0–2;

AA is the aminocarboxylic acid glycine or alanine;

Y is

1) $(C_2-C_5)$-alkenediyl,
2) $(C_2-C_4)$-alkanediyl,
3) $(C_3-C_6)$-cycloalkanediyl or
4) $-(CH_2)_p-T_o-(CH_2)_q-$;

T is O or S;

o is a number 0 or 1;

p and q are identical or different, and are a number from 0–2;

$R^{15}$ is 1) hydrogen,
2) $(C_1-C_5)$-alkyl,
3) phenyl or
4) $(C_5-C_9)$-heteroaryl, where 3) and 4) can optionally be substituted by one, two or three identical or different groups, such as halogen, $NO_2$, $(C_1-C_3)$-alkylthio, $NR^{20}R^{21}$, $NR^{20}CO-(C_1-C_5)$-alkyl and $NR^{20}CO$-pyridyl, $(C_1-C_3)$-alkyl or $(C_1-C_3)$-alkoxy, in which, if appropriate, the hydrogen atoms of the alkyl or alkoxy group can be partly or completely replaced by halogen;

$R^{16}$ is hydrogen, $(C_1-C_4)$-alkyl or phenyl;

$R^{17}$ is hydrogen, halogen, $(C_1-C_4)$-alkyl, $NO_2$or $NH_2$;

$R^{20}$ is independently hydrogen, $(C_1-C_4)$-alkyl or benzyl;

$R^{21}$ is independently hydrogen or $C(O)-O-(C_1-C_4)$-alkyl;

Z is $-N(R^{14})(R^{22})$;

$R^{22}$ is

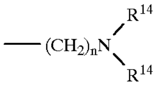

or

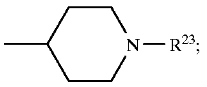

$R^{23}$ is $(CO_1-C_4)$-alkyl,

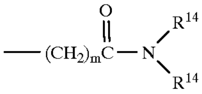

or

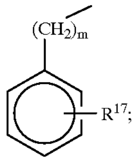

or a physiologically tolerable salt thereof.

4. The method as claimed in claim 2, in which said non-peptide bradykinin antagonist of the formula (I), wherein:

D is 1) a radical of the formula (Xa)

(Xa)

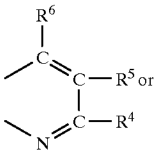

2) a radical of the formula (Xb)

(Xb)

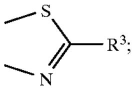

E is a radical of the formula (XI)

(XI)

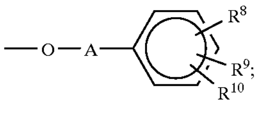

$R^1$ and $R^2$ are identical or different, and are hydrogen, halogen or $(C_1-C_4)$-alkyl;

$R^4$ is hydrogen or $(C_1-C_4)$-alkyl;

$R^5$ is hydrogen;

$R^6$ is hydrogen;

$R^8$ and $R^9$ are identical or different, and are hydrogen, chlorine, methyl or methoxy;

A is $-CH_2-$ or $-CH_2-CH_2-$;

$R^{10}$ is a radical of the formula (IX)

(IX)

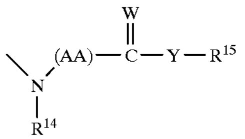

W is oxo;

$R^{14}$ is hydrogen, methyl or ethyl;

AA is the aminocarboxylic acid glycine;

Y is

1) $(C_2-C_5)$-alkenediyl,
2) $(C_2-C_4)$-alkanediyl,
3) $(C_3-C_6)$-cycloalkanediyl or
4) $-(CH_2)_p-T_o-(CH_2)_q-$;

T is O or S;

o is a number 0 or 1;

p and q are identical or different, and are a number from 0–2;

$R^{15}$ is 1) is hydrogen
2) $(C_1-C_3)$-alkyl,
3) phenyl or
4) $(C_5-C_9)$-heteroaryl, where 3) and 4) can optionally be substituted by one, two or three identical or different groups, such as halogen, $NO_2$, $NR^{20}R^{21}$, $NR^{20}CO-(C_1-C_3)$-alkyl and $NR^{20}CO$-pyridyl, $(C_1-C_3)$-alkyl or $(C_1-C_3)$-alkoxy, in which, if appropriate, the hydrogen atoms of the alkyl or alkoxy group are partly or completely replaced by halogen;

$R^{20}$ is independently hydrogen, $(C_1-C_4)$-alkyl or benzyl;

$R^{21}$ is hydrogen or $C(O)-O-(C_1-C_5)$-alkyl; or a physiologically tolerable salt thereof.

5. The method as claimed in claim 1, wherein said non-peptide bradykinin antagonist is:

N-{1-{4-(1,1-dimethylethyl)phenyl}methyl4-piperidinyl}-8-methoxy-4-{{4-{{{1-(phenylmethyl)4-piperidinyl}amino}carbonyl}phenylamino}3-quinolinecarboxamide;

N-{1 -{(3-chlorophenyl}methyl-4-piperidinyl}-8-methoxy-4-{{4-{{{1-(phenylmethyl)-4-piperidinyl}amino}carbonyl}phenylamino}3-quinolinecarboxamide;

8-methoxy-N-{1-(phenyl}methyl-4-piperidinyl-{4-{{4-{{{1-(phenylmethyl)-4-piperidinyl}amino}carbonyl} phenylamino}-3-quinolinecarboxamide;

N-{2-(dimethylamino)ethyl}8-methoxy-4-{{4-{{{1-(phenylmethyl)4-piperidinyl}amino}carbonyl} phenylamino}-3-quinolinecarboxamide trifluoroacetate;

N-2-(dimethylamino)ethyl}-N-ethyl-8-methoxy-4-{{4-{{{1-(phenylmethyl)4-piperidinyl}amino}carbonyl} phenylamino}3-quinolinecarboxamide;

4-{{4-{{(3-cyclopentyl-1-oxopropyl)-{1-{6-(diethylamino)-6-oxo-hexyl-4-piperidinylamino} methylphenyl}amino}-8-methoxy- N-{1-(phenylmethyl)4-piperidinyl}-3-quinolinecarboxamide;

4-(4-{{(1-butyl4-piperidinylamino}methyl}phenyl-amino}-8-methoxy-N-1-(phenylmethyl)4-piperidinyl}-3-quinolinecarboxamide;

N-(1-butyl4-piperidinyl)-8-methoxy-{{4-{{{1-(phenylmethyl)-4-piperidinyl}amino}carbonyl} phenyl}amino-3-quinolinecarboxamide;

N-1-6-(diethylamino)-6-oxohexyl-4-piperidinyl-8-methoxy-4-{{4-{{{1-(phenylmethyl)-4-piperidinyl}amino}carbonyl}phenyl}amino}3-quinolinecarboxamide;

4-{{4-{{(1-butyl-4-piperidinyl)-(1-oxobutyl) amino}methyl}phenyl}amino-3-methoxy-N-{1-(phenylmethyl)-4-piperidinyl}-3-quinolinecarboxamide;

N-{1-{4-{(diethylamino)carbonyl}phenyl4-piperidinyl-8-methoxy-4-{{4-{{{1-(phenylmethyl)-4-piperidinyl}amino}carbonyl}phenyl}amino-3-quinolinecarboxamide;

N-{1-(2-phenylethyl)4-piperidinyl}-8-methoxy-4-{{4-{{{1-(phenylmethyl)-4-piperidinyl}amino}carbonyl} phenyl}amino}-3-quinolinecarboxamide;

4-{{4-{{(1-butyl4-piperidinyl)amino}carbonyl}-phenyl}amino}-8-methoxy-N-{1-(phenylmethyl)4-piperidinyl}-3-quinolinecarboxamide;

8-methoxy-N-(1-methyl-4-piperidinyl)-4-{{4-{{{1-(phenylmethyl)-4-piperidinyl}amino}carbonyl} phenyl}amino}-3-quinolinecarboxamide;

N-1-{(3-methoxyphenyl)methyl}4-piperidinyl-8-methoxy-4-{{4-{{{1-(phenylmethyl)-4-piperidinyl}amino}carbonyl}phenyl}-amino-3-quinolinecarboxamide;

8-methoxy-4-{{4-{{{1-(phenylmethyl)4-piperidinyl}amino}carbonyl}phenyl}-amino}-1-{{3-(trifluoromethyl)phenyl}methyl}-4-piperidinyl)-3-quinolinecarboxamide;

7-chloro-N-{1-(phenylmethyl)-4-piperidinyl}-4-{{4-{{{1-(phenylmethyl)-4-piperidinyl}amino}carbonyl} phenyl}amino-3-quinolinecarboxamide;

or a physiologically tolerable salt thereof.

* * * * *

UNITED STATES PATENT AND TRADEMARK OFFICE

CERTIFICATE OF CORRECTION

PATENT NO. : 5,952,346 
DATED : September 14, 1999
INVENTOR(S) : Holger Heitsch et al.

It is certified that error appears in the above-identified patent and that said Letters Patent is hereby corrected as shown below:

Title page,
Line [57], ABSTRACT,
Line 4, "Compounds" should read -- compounds --.
Line 6, "such as" should read -- such as, --.

Column 48,
Lines 2 and 3, "($C_1$-$C_5$)-alkenyl" should read -- ($C_3$-$C_5$)-alkenyl --.

Column 49,
Line 25, "(O-$R^8$)" should read -- O-$R^{18}$ --.
Line 29, "O or 1" should read -- 0 or 1 --.
Line 41, "$SO_2R^{18,}$" should read $SO_2R^{18}$, --.
Line 59, "($R:^{14}$)" should read -- ($R^{14}$) --.

Column 52,
Line 1, "$NO_2$or" should read -- $NO_2$ or --.
Line 3, "($C_1$-$C_4$)" should read -- ($C_1$-$C_5$) --.
Line 15, "($CO_1$-$C_4$)" should read -- ($C_1$-$C_4$) --.

Column 53,
Line 41, "methyl4" should read -- methy1-4- --.
Line 42, "(phenylmethyl)" should read -- (phenylmethyl)- --.
Line 43, "phenylamino}3-" should read -- phenylamino}-3- --.
Line 52, "ethyl}8-" should read -- ethyl}-8- --.
Line 53, "(phenylmethyl)4-" should read -- phenylmethyl-4- --.

UNITED STATES PATENT AND TRADEMARK OFFICE

CERTIFICATE OF CORRECTION

PATENT NO. : 5,952,346
DATED : September 14, 1999
INVENTOR(S) : Holger Heitsch et al.

It is certified that error appears in the above-identified patent and that said Letters Patent is hereby corrected as shown below:

Column 54,
Line 2, "(phenylmethyl)4-" should read -- phenylmethyl)-4- --.
Line 3, "phenylamino}3-" should read -- phenylamino}-3- --.
Line 5, "4-{{(3-" should read -- 4-{{{(3- --.
Line 7, "methoxy– N" should read -- methoxy-N --.
Line 8, "(phenylmethyl)4-" should read -- (phenylmethyl)-4- --.
Line 10, "4-(4-" should read -- 4-{{4- --.
Line 10, "butyl4" should read -- buty1-4 --.
Line 11, "-N-" should read -- -N-{ --.
Line 11, "(phenylmethyl)4-" should read -- (phenylmethyl)-4- --.
Line 14, "1-butyl4" should read -- 1-butyl-4 --.
Line 16, "amino-3" should read -- amino}-3 --.
Line 17, "N-1" should read -- N-{1 --.
Line 17, "N-1" should read -- N-{1 --.
Line 20, "amino}3-" should read -- amino}-3- --.
Line 23, "amino-3" should read -- amino-{8 --.
Line 24, "quinolinecarboxam" should read -- quinolinecarboxam- --.
Line 26, "phenyl4" should read -- phenyl-4 --.
Line 30, "4-piperidinyl" should read -- -4-piperidinyl --.
Line 34, "butyl4" should read -- butyl-4 --.

Signed and Sealed this

Third Day of September, 2002

*Attest:*

JAMES E. ROGAN

*Attesting Officer*

*Director of the United States Patent and Trademark Office*